(12) United States Patent
Kubota et al.

(10) Patent No.: US 11,779,206 B2
(45) Date of Patent: Oct. 10, 2023

(54) AXIAL LENGTH MEASUREMENT MONITOR

(71) Applicant: ACUCELA INC., Seattle, WA (US)

(72) Inventors: Ryo Kubota, Seattle, WA (US); Philip M. Buscemi, Mount Pleasant, SC (US); Matthias Pfister, Liebefeld-Bern (CH); Stephan Wyder, Bern (CH); Amitava Gupta, Roanoke, VA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/936,263

(22) Filed: Sep. 28, 2022

(65) Prior Publication Data
US 2023/0026753 A1    Jan. 26, 2023

Related U.S. Application Data

(63) Continuation of application No. 17/647,585, filed on Jan. 10, 2022, now Pat. No. 11,497,396.
(Continued)

(51) Int. Cl.
*G01B 9/02* (2022.01)
*A61B 3/10* (2006.01)
*G01B 9/02091* (2022.01)

(52) U.S. Cl.
CPC .......... *A61B 3/102* (2013.01); *G01B 9/02091* (2013.01); *G01B 2290/45* (2013.01)

(58) Field of Classification Search
CPC ........................... A61B 3/102; G01B 9/02027; G01B 9/02028; G01B 9/02091; G01B 2290/45
See application file for complete search history.

(56) References Cited

U.S. PATENT DOCUMENTS

| 5,255,274 A | 10/1993 | Wysocki |
| 5,396,325 A | 3/1995 | Carome |

(Continued)

FOREIGN PATENT DOCUMENTS

| CA | 3111012 | 1/2021 |
| CN | 105188540 | 12/2015 |

(Continued)

OTHER PUBLICATIONS

Bengio, Yoshua, et al., "Curriculum Learning," 8 pages, retrieved from http://machinelearning.org/archive/icml2009/papers/119.pdf on Jun. 14, 2021.
(Continued)

*Primary Examiner* — Uzma Alam
*Assistant Examiner* — Jonathon Cook
(74) *Attorney, Agent, or Firm* — FISHERBROYLES LLP; John Shimmick

(57) ABSTRACT

An OCT axial length measurement device is configured to measure an area of the retina within a range from about 0.05 mm to about 2.0 mm. The area can be measured with a scanned measurement beam or plurality of substantially fixed measurement beams. The OCT measurement device may comprise a plurality of reference optical path lengths, in which a first optical path length corresponds to a first position of a cornea, and a second optical path length corresponds to a second position of the retina, in which the axial length is determined based on a difference between the first position and the second position. An axial length map can be generated to determine alignment of the eye with the measurement device and improve accuracy and repeatability of the measurements. In some embodiments, the OCT measurement device comprises a swept source vertical cavity surface emitting laser ("VCSEL").

19 Claims, 19 Drawing Sheets

Related U.S. Application Data

(60) Provisional application No. 63/200,718, filed on Mar. 24, 2021.

(56) References Cited

U.S. PATENT DOCUMENTS

| | | | |
|---|---|---|---|
| 6,053,613 | A | 4/2000 | Wei |
| 6,325,512 | B1 | 12/2001 | Wei |
| 6,362,919 | B1 | 3/2002 | Flanders |
| 6,409,395 | B1 | 6/2002 | Wang |
| 6,419,360 | B1 | 7/2002 | Hauger |
| 6,445,944 | B1 | 9/2002 | Ostrovsky |
| 6,552,796 | B2 | 4/2003 | Magnin |
| 6,726,325 | B2 | 4/2004 | Xie |
| 6,736,508 | B2 | 5/2004 | Xie |
| 6,769,769 | B2 | 8/2004 | Podoleanu |
| 6,778,307 | B2 | 8/2004 | Clark |
| 7,113,818 | B2 | 9/2006 | Podoleanu |
| 7,126,693 | B2 | 10/2006 | Everett |
| 7,140,730 | B2 | 11/2006 | Wei |
| 7,301,644 | B2 | 11/2007 | Knighton |
| 7,324,569 | B2 | 1/2008 | Flanders |
| 7,347,548 | B2 | 3/2008 | Huang |
| 7,375,818 | B2 | 5/2008 | Kawahara |
| 7,391,520 | B2 | 6/2008 | Zhou |
| 7,452,077 | B2 | 11/2008 | Meyer |
| 7,482,589 | B2 | 1/2009 | Flanders |
| 7,542,145 | B2 | 6/2009 | Toida |
| 7,594,730 | B2 | 9/2009 | Podoleanu |
| 7,602,500 | B2 | 10/2009 | Izatt |
| 7,633,623 | B2 | 12/2009 | Hatori |
| 7,633,627 | B2 | 12/2009 | Choma |
| 7,701,585 | B2 | 4/2010 | Hatori |
| 7,761,139 | B2 | 7/2010 | Tearney |
| 7,783,337 | B2 | 8/2010 | Feldman |
| 7,864,335 | B2 | 1/2011 | Terakawa |
| 7,872,759 | B2 | 1/2011 | Tearney |
| 7,929,148 | B2 | 4/2011 | Kemp |
| 7,954,947 | B2 | 6/2011 | Sugita |
| 7,971,999 | B2 | 7/2011 | Zinser |
| 7,980,694 | B2 | 7/2011 | Keating |
| 7,980,696 | B1 | 7/2011 | Taki |
| 7,997,728 | B2 | 8/2011 | Huang |
| 7,997,729 | B2 | 8/2011 | Mclean |
| 8,025,403 | B2 | 9/2011 | Maloca |
| 8,049,900 | B2 | 11/2011 | Kemp |
| 8,055,107 | B2 | 11/2011 | Masuda |
| 8,079,711 | B2 | 12/2011 | Stetson |
| 8,123,354 | B2 | 2/2012 | Olivier |
| 8,139,226 | B2 | 3/2012 | Johnson |
| 8,192,024 | B2 | 6/2012 | Yumikake |
| 8,205,991 | B2 | 6/2012 | Wei |
| 8,220,924 | B2 | 7/2012 | Hanebuchi |
| 8,251,510 | B2 | 8/2012 | Kobayashi |
| 8,251,511 | B2 | 8/2012 | Stetson |
| 8,282,211 | B2 | 10/2012 | Campbell |
| 8,289,522 | B2 | 10/2012 | Tearney |
| 8,348,427 | B2 | 1/2013 | Buckland |
| 8,348,429 | B2 | 1/2013 | Walsh |
| 8,351,665 | B2 | 1/2013 | Tearney |
| 8,363,783 | B2 | 1/2013 | Gertner |
| 8,403,481 | B2 | 3/2013 | Izatt |
| 8,405,834 | B2 | 3/2013 | Srinivasan |
| 8,421,855 | B2 | 4/2013 | Buckland |
| 8,425,037 | B2 | 4/2013 | Uhlhorn |
| 8,442,284 | B2 | 5/2013 | Rogers |
| 8,446,593 | B1 | 5/2013 | Ellerbee |
| 8,457,440 | B1 | 6/2013 | Johnson |
| 8,467,051 | B2 | 6/2013 | Flanders |
| 8,474,978 | B2 | 7/2013 | Huang |
| 8,500,279 | B2 | 8/2013 | Everett |
| 8,526,006 | B2 | 9/2013 | Nebosis |
| 8,529,062 | B2 | 9/2013 | Buckland |
| 8,594,757 | B2 | 11/2013 | Boppart |
| 8,608,314 | B2 | 12/2013 | Yoon |
| 8,630,697 | B2 | 1/2014 | Meyer |
| 8,665,450 | B2 | 3/2014 | Johnson |
| 8,711,366 | B2 | 4/2014 | Everett |
| 8,721,078 | B2 | 5/2014 | Torii |
| 8,724,870 | B2 | 5/2014 | Sekine |
| 8,757,803 | B2 | 6/2014 | Everett |
| 8,781,287 | B2 | 7/2014 | Flanders |
| 8,794,763 | B2 | 8/2014 | Stetson |
| 8,801,184 | B2 | 8/2014 | Hacker |
| 8,820,931 | B2 | 9/2014 | Walsh |
| 8,836,953 | B2 | 9/2014 | Johnson |
| 8,870,376 | B2 | 10/2014 | Hogan |
| 8,894,207 | B2 | 11/2014 | Hee |
| 8,913,248 | B2 | 12/2014 | Sharma |
| 8,922,782 | B2 | 12/2014 | Flanders |
| 8,926,097 | B2 | 1/2015 | Sakagawa |
| 8,939,582 | B1 | 1/2015 | Spaide |
| 8,947,648 | B2 | 2/2015 | Swanson |
| 8,953,167 | B2 | 2/2015 | Johnson |
| 8,971,360 | B2 | 3/2015 | Lewandowski |
| 8,992,018 | B2 | 3/2015 | Makihira |
| 8,994,753 | B2 | 3/2015 | Nakano |
| 8,998,412 | B2 | 4/2015 | Makihira |
| 9,016,862 | B2 | 4/2015 | Carnevale |
| 9,025,160 | B2 | 5/2015 | Moore |
| 9,025,847 | B2 | 5/2015 | Kitamura |
| 9,033,504 | B2 | 5/2015 | Everett |
| 9,033,510 | B2 | 5/2015 | Narasimha-Iyer |
| 9,044,164 | B2 | 6/2015 | Hacker |
| 9,055,891 | B2 | 6/2015 | Suehira |
| 9,055,892 | B2 | 6/2015 | Narasimha-Iyer |
| 9,060,689 | B2 | 6/2015 | Tearney |
| 9,084,562 | B2 | 7/2015 | Kakuma |
| 9,095,281 | B2 | 8/2015 | Sharma |
| 9,119,562 | B2 | 9/2015 | Naba |
| 9,138,141 | B2 | 9/2015 | Makihira |
| 9,144,378 | B2 | 9/2015 | Suehira |
| 9,149,182 | B2 | 10/2015 | Walsh |
| 9,161,690 | B2 | 10/2015 | Tomatsu |
| 9,163,929 | B2 | 10/2015 | Lim |
| 9,163,930 | B2 | 10/2015 | Buckland |
| 9,167,964 | B2 | 10/2015 | Everett |
| 9,171,367 | B2 | 10/2015 | Iwase |
| 9,176,319 | B2 | 11/2015 | Bouma |
| 9,178,330 | B2 | 11/2015 | Oh |
| 9,192,294 | B2 | 11/2015 | Sharma |
| 9,200,888 | B2 | 12/2015 | Jaillon |
| 9,217,707 | B2 | 12/2015 | Bajraszewski |
| 9,226,653 | B2 | 1/2016 | Torii |
| 9,226,660 | B2 | 1/2016 | De Boer |
| 9,241,626 | B2 | 1/2016 | Narasimha-Iyer |
| 9,243,885 | B2 | 1/2016 | Johnson |
| 9,259,151 | B2 | 2/2016 | Murase |
| 9,267,783 | B1 | 2/2016 | Sharma |
| 9,273,950 | B2 | 3/2016 | Yazdanfar |
| 9,291,446 | B2 | 3/2016 | Schneider |
| 9,310,182 | B2 | 4/2016 | Goldberg |
| 9,339,186 | B2 | 5/2016 | Somani |
| 9,354,038 | B2 | 5/2016 | Yasuno |
| 9,373,933 | B2 | 6/2016 | Njegovec |
| 9,375,158 | B2 | 6/2016 | Vakoc |
| 9,377,293 | B2 | 6/2016 | Hauger |
| 9,380,935 | B2 | 7/2016 | Iwase |
| 9,408,532 | B2 | 8/2016 | Makihira |
| 9,427,147 | B2 | 8/2016 | Lujan |
| 9,427,150 | B2 | 8/2016 | Muto |
| 9,433,353 | B2 | 9/2016 | Hanebuchi |
| 9,468,374 | B2 | 10/2016 | Makihira |
| 9,492,077 | B2 | 11/2016 | Ebersbach |
| 9,492,079 | B2 | 11/2016 | Walsh |
| 9,526,412 | B2 | 12/2016 | Yang |
| 9,526,415 | B2 | 12/2016 | Fukuma |
| 9,526,425 | B2 | 12/2016 | Feldman |
| 9,532,713 | B2 | 1/2017 | Levecq |
| 9,545,199 | B2 | 1/2017 | Wang |
| 9,584,098 | B2 | 2/2017 | Yamanari |
| 9,612,105 | B2 | 4/2017 | Kemp |
| 9,615,736 | B2 | 4/2017 | Yamashita |
| 9,633,424 | B2 | 4/2017 | Nebosis |
| 9,649,024 | B2 | 5/2017 | Hacker |

(56) References Cited

U.S. PATENT DOCUMENTS

| | | |
|---|---|---|
| 9,649,025 B2 | 5/2017 | Jeglorz |
| 9,671,620 B2 | 6/2017 | Gupta |
| 9,696,132 B2 | 7/2017 | Jayaraman |
| 9,702,686 B2 | 7/2017 | Hattersley |
| 9,778,018 B2 | 10/2017 | Schmoll |
| 9,778,020 B2 | 10/2017 | Tumlinson |
| 9,784,559 B2 | 10/2017 | Huber |
| 9,812,846 B2 | 11/2017 | Yun |
| 9,869,542 B2 | 1/2018 | Goldberg |
| 9,897,538 B2 | 2/2018 | Tearney |
| 9,915,520 B2 | 3/2018 | Cable |
| 9,939,659 B2 | 4/2018 | Gupta |
| 9,948,061 B2 | 4/2018 | Njegovec |
| 9,977,184 B1 | 5/2018 | Wong |
| 9,978,159 B2 | 5/2018 | Kraus |
| 9,993,153 B2 | 6/2018 | Chong |
| 10,045,692 B2 | 8/2018 | Tumlinson |
| 10,049,470 B2 | 8/2018 | Pintal |
| 10,098,537 B2 | 10/2018 | Iwase |
| 10,114,232 B2 | 10/2018 | Gupta |
| 10,327,631 B2 | 6/2019 | Huang |
| 10,413,175 B2 | 9/2019 | Yun |
| 10,478,058 B2 | 11/2019 | Cheng |
| 10,568,501 B2 | 2/2020 | Boss |
| 10,595,723 B2 | 3/2020 | Meznaric |
| 10,610,096 B2 | 4/2020 | Scheibler |
| 10,912,456 B2 | 2/2021 | Brennan |
| 10,952,607 B2 | 3/2021 | Scheibler |
| 10,959,613 B1 | 3/2021 | Kubota |
| 11,357,401 B2 | 6/2022 | Oggenfuss et al. |
| 11,369,266 B2 | 6/2022 | Kubota |
| 11,393,094 B2 | 7/2022 | Wyder |
| 11,497,396 B2 | 11/2022 | Kubota |
| 2003/0011745 A1 | 1/2003 | Molebny |
| 2004/0246441 A1 | 12/2004 | Stark |
| 2004/0257529 A1 | 12/2004 | Thomas |
| 2005/0018133 A1 | 1/2005 | Huang |
| 2005/0140981 A1 | 6/2005 | Waelti |
| 2006/0131488 A1 | 6/2006 | Thingbo |
| 2006/0152106 A1 | 7/2006 | Yan |
| 2006/0244339 A1 | 11/2006 | Mazz |
| 2007/0002452 A1 | 1/2007 | Munro |
| 2007/0076217 A1 | 4/2007 | Baker |
| 2007/0127349 A1 | 6/2007 | Hotta |
| 2007/0183643 A1 | 8/2007 | Jayaraman |
| 2007/0230856 A1 | 10/2007 | Yamazaki |
| 2007/0263171 A1 | 11/2007 | Ferguson |
| 2008/0100612 A1 | 5/2008 | Dastmalchi |
| 2008/0117427 A1 | 5/2008 | Teramura |
| 2008/0181263 A1 | 7/2008 | Bouma |
| 2008/0296480 A1 | 12/2008 | Haber |
| 2009/0002631 A1 | 1/2009 | Campbell |
| 2009/0123044 A1 | 5/2009 | Huang |
| 2009/0141237 A1 | 6/2009 | Izatt |
| 2009/0244485 A1 | 10/2009 | Walsh |
| 2010/0110376 A1 | 5/2010 | Everett |
| 2010/0110377 A1 | 5/2010 | Maloca |
| 2011/0043757 A1 | 2/2011 | Everett |
| 2011/0080561 A1 | 4/2011 | Hayashi |
| 2011/0157554 A1 | 6/2011 | Kawai |
| 2011/0164633 A1 | 7/2011 | Moench |
| 2011/0299034 A1 | 12/2011 | Walsh |
| 2012/0033227 A1 | 2/2012 | Bower |
| 2012/0092616 A1 | 4/2012 | Peyman |
| 2012/0300216 A1 | 11/2012 | Johnson |
| 2012/0327365 A1 | 12/2012 | Makihira |
| 2013/0010259 A1 | 1/2013 | Carnevale |
| 2013/0010302 A1 | 1/2013 | Sharma |
| 2013/0016360 A1 | 1/2013 | Ensher |
| 2013/0103014 A1 | 4/2013 | Gooding |
| 2013/0158392 A1 | 6/2013 | Papac |
| 2013/0235343 A1 | 9/2013 | Hee |
| 2013/0250241 A1 | 9/2013 | Everett |
| 2014/0028997 A1 | 1/2014 | Cable |
| 2014/0112562 A1 | 4/2014 | Yamakawa |
| 2014/0121508 A1 | 5/2014 | Latimer |
| 2014/0125987 A1 | 5/2014 | Flanders |
| 2014/0218745 A1 | 8/2014 | Hattersley |
| 2014/0241605 A1 | 8/2014 | Izatt |
| 2014/0268050 A1 | 9/2014 | Jayaraman |
| 2014/0268169 A1 | 9/2014 | Jayaraman |
| 2014/0269796 A1 | 9/2014 | Geske |
| 2014/0285812 A1 | 9/2014 | Levitz |
| 2014/0307078 A1 | 10/2014 | Charles |
| 2014/0307753 A1 | 10/2014 | Minneman |
| 2014/0340689 A1 | 11/2014 | Namati |
| 2014/0347632 A1 | 11/2014 | Mordaunt |
| 2015/0010031 A1 | 1/2015 | Makino |
| 2015/0018674 A1 | 1/2015 | Scott |
| 2015/0055089 A1 | 2/2015 | Aono |
| 2015/0062532 A1 | 3/2015 | Sharma |
| 2015/0085253 A1 | 3/2015 | Walsh |
| 2015/0109579 A1 | 4/2015 | Orlowski |
| 2015/0110376 A1 | 4/2015 | Gessner |
| 2015/0198431 A1 | 7/2015 | Uchida |
| 2015/0216408 A1 | 8/2015 | Brown |
| 2015/0216412 A1 | 8/2015 | Hillmann |
| 2015/0230705 A1* | 8/2015 | Kato ................. G01B 9/02004 |
| | | 351/206 |
| 2015/0327761 A1 | 11/2015 | Narasimha-Iyer |
| 2015/0327762 A1 | 11/2015 | Isogai |
| 2016/0000368 A1 | 1/2016 | Wang |
| 2016/0007857 A1 | 1/2016 | Wang |
| 2016/0025478 A1 | 1/2016 | Johnson |
| 2016/0040976 A1 | 2/2016 | Berkeley |
| 2016/0040977 A1 | 2/2016 | An |
| 2016/0040978 A1 | 2/2016 | Boppart |
| 2016/0081545 A1 | 3/2016 | Hauger |
| 2016/0082129 A1 | 3/2016 | Peters |
| 2016/0106310 A1 | 4/2016 | Moriguchi |
| 2016/0106312 A1 | 4/2016 | Moriguchi |
| 2016/0106314 A1 | 4/2016 | Everett |
| 2016/0128565 A1 | 5/2016 | Meznaric |
| 2016/0166143 A1 | 6/2016 | Goto |
| 2016/0206190 A1 | 7/2016 | Reisman |
| 2016/0212404 A1 | 7/2016 | Maiello |
| 2016/0242638 A1 | 8/2016 | Durbin |
| 2016/0252340 A1 | 9/2016 | Hollenbeck |
| 2016/0262609 A1 | 9/2016 | Cai |
| 2016/0270656 A1 | 9/2016 | Samec |
| 2016/0321828 A1 | 11/2016 | Tachikawa |
| 2016/0338589 A1 | 11/2016 | Carrasco-Zevallos |
| 2016/0367129 A1 | 12/2016 | Coelho |
| 2016/0367132 A1 | 12/2016 | Yun |
| 2017/0007182 A1 | 1/2017 | Samec |
| 2017/0020387 A1 | 1/2017 | Fingler |
| 2017/0049318 A1 | 2/2017 | Walsh |
| 2017/0055829 A1 | 3/2017 | Tan |
| 2017/0065169 A1 | 3/2017 | Fukasawa |
| 2017/0074640 A1 | 3/2017 | Cable |
| 2017/0102223 A1 | 4/2017 | Izatt |
| 2017/0105618 A1 | 4/2017 | Schmoll |
| 2017/0140560 A1 | 5/2017 | Kraus |
| 2017/0156583 A1 | 6/2017 | Seesselberg |
| 2017/0205223 A1 | 7/2017 | Cable |
| 2017/0227350 A1 | 8/2017 | Sarunic |
| 2017/0231489 A1 | 8/2017 | Fujimori |
| 2017/0236255 A1 | 8/2017 | Wetzstein |
| 2017/0241763 A1 | 8/2017 | Wang |
| 2017/0258321 A1 | 9/2017 | Dastmalchi |
| 2017/0268987 A1 | 9/2017 | Swanson |
| 2017/0276471 A1 | 9/2017 | Jiang |
| 2017/0280993 A1 | 10/2017 | Fukuhara |
| 2017/0311795 A1 | 11/2017 | Sumiya |
| 2017/0356740 A1 | 12/2017 | Ansari |
| 2018/0012359 A1 | 1/2018 | Prentasic |
| 2018/0031363 A1 | 2/2018 | Johnson |
| 2018/0051978 A1 | 2/2018 | Flanders |
| 2018/0055358 A1 | 3/2018 | Nakajima |
| 2018/0064331 A1 | 3/2018 | Naba |
| 2018/0084994 A1 | 3/2018 | Su |
| 2018/0125354 A1 | 5/2018 | Pulaski |
| 2018/0135962 A1 | 5/2018 | Murata |
| 2018/0156598 A1 | 6/2018 | Cable |

(56) References Cited

U.S. PATENT DOCUMENTS

| | | |
|---|---|---|
| 2018/0157924 A1 | 6/2018 | Hogan |
| 2018/0168445 A1 | 6/2018 | Horn |
| 2018/0206716 A1 | 7/2018 | Chong |
| 2018/0271363 A1 | 9/2018 | Scheibler |
| 2018/0289256 A1 | 10/2018 | Murata |
| 2019/0365220 A1 | 12/2019 | Frisken |
| 2019/0380574 A1 | 12/2019 | Chen |
| 2020/0093363 A1 | 3/2020 | Saika |
| 2020/0196858 A1 | 6/2020 | Scheibler |
| 2020/0234080 A1 | 7/2020 | Ciller Ruiz |
| 2020/0342595 A1 | 10/2020 | Jia |
| 2020/0372632 A1 | 11/2020 | Chauhan |
| 2021/0127969 A1 | 5/2021 | Oggenfuss |
| 2021/0196113 A1* | 7/2021 | Copland ............ A61B 3/145 |
| 2021/0386285 A1* | 12/2021 | Walsh ............ A61B 3/113 |

FOREIGN PATENT DOCUMENTS

| | | |
|---|---|---|
| CN | 105263415 | 1/2016 |
| CN | 105792728 | 7/2016 |
| DE | 102016121246 | 5/2018 |
| EP | 2725508 | 4/2014 |
| EP | 2759254 | 7/2014 |
| EP | 2892413 | 7/2015 |
| JP | 201172716 | 4/2011 |
| JP | 201483266 | 5/2014 |
| JP | 2016514828 | 5/2016 |
| WO | 9320743 | 10/1993 |
| WO | 2009120544 | 10/2009 |
| WO | 2010117386 | 10/2010 |
| WO | 2015082001 | 6/2015 |
| WO | 2015116981 | 8/2015 |
| WO | 2015120055 | 8/2015 |
| WO | 2015192117 | 12/2015 |
| WO | 2016040534 | 3/2016 |
| WO | 2016073840 | 5/2016 |
| WO | 2016115387 | 7/2016 |
| WO | 2016125474 | 8/2016 |
| WO | 2016127140 | 8/2016 |
| WO | 2016148569 | 9/2016 |
| WO | 2016178298 | 11/2016 |
| WO | 2016179431 | 11/2016 |
| WO | 2016196463 | 12/2016 |
| WO | 2016203245 | 12/2016 |
| WO | 2017002379 | 1/2017 |
| WO | 2017025583 | 2/2017 |
| WO | 2017046225 | 3/2017 |
| WO | 2017048832 | 3/2017 |
| WO | 2017165793 | 9/2017 |
| WO | 2017176301 | 10/2017 |
| WO | 2017206929 | 12/2017 |
| WO | 2017216242 | 12/2017 |
| WO | 2018086173 | 5/2018 |
| WO | 2018089682 | 5/2018 |
| WO | 2018105549 | 6/2018 |
| WO | 2018116128 | 6/2018 |
| WO | 2018119077 | 6/2018 |
| WO | 2019210079 | 10/2019 |
| WO | 2019246412 | 12/2019 |
| WO | 2020036182 | 2/2020 |
| WO | 2020160839 A1 | 8/2020 |
| WO | 2021134087 | 7/2021 |
| WO | 2022032260 | 2/2022 |
| WO | 2022035809 | 2/2022 |
| WO | 2022056515 | 3/2022 |
| WO | 2022204622 | 9/2022 |

OTHER PUBLICATIONS

Bertera, J.H., et al., "Stabilized Retinal Mapping of Known Retinal Loci," Proceedings of the Annual Northeast Bioengineering Conference, IEEE, vol. Conf. 14, No. 1988, XP000010509 (Mar. 10, 1988).

Girish et al. Segmentation of Intra-Retinal Cysts From Optical Coherence Tomography Images Using a Fully Convolutional Neural Network Model. IEEE Journal of Biomedical and Health Informatics, vol. 23, No. 1, Jan. 2019, pp. 296-304 (Year: 2019).

Haglund, Erik, et al., "Multi-wavelength VCSEL arrays using high-contrast gratings," Proc. of SPIE vol. 10113, 7 pages (2017).

Huang, et al., "Optical coherence tomograph," Science, 254(5035):1178-1181 (Nov. 22, 1991).

Huang, Huimin, et al., "UNET 3+: A Full-Scale Connected UNET for Medical Image Segmentation," 5 pages, retrieved from https://arxiv.org/ftp/arxiv/papers/2004/2004.08790.pdf on Jun. 14, 2021.

International Search Report and Written Opinion for PCT/US2022/070125, 11 pages (dated Jun. 9, 2022).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Khan, Zuhaib, et al., "High-brightness and high-speed vertical-cavity surface-emitting laser arrays," Optica, 7(4):267-275 (Apr. 2020).

Kolb, Jan Philip, et al., "High-resolution retinal swept source optical coherence tomography with an ultra-wideband Fourier-domain mode-locked laser at MHz A-scan rates," Biomedical Optics Express, 9(1):120-130 (2018).

Mishra, Z., et al., "Automated Retinal Layer Segmentation Using Graph-based Algorithm Incorporating Deep-learning-derived Information," Sci Rep. 10(1):9541 (2020).

Moon, S., et al., "VCSEL-based swept source for low-cost optical coherence tomography", Biomedical Optics Express, 8(2):1110-1121 (Feb. 1, 2017).

ORR. Notal Vision—Home-Based Optical Coherence Tomograph (OCT). Slide deck (11 pgs.) (Nov. 9, 2017).

Pierro, L., et al., "Macular Thickness Interoperator and Intraoperator Reproducibility in Healthy Eyes Using 7 Optical Coherence Tomography Instruments," American Journal of Ophthalmology, 150(2): 199-204, XP027174249 (Aug. 1, 2010).

Sanghoon, Kim, et al., "Design and implementation of a low-cost, portable OCT system," 9(3):1232-1243 (Mar. 1, 2018).

WO 2020/036182 A1 machine translation from Japanese to English (132 pages).

Zara, J.M., et al., "Electrostatic micromachine scanning mirror for optical coherence tomography," Optics Letters, 28(8):628-630 (Apr. 15, 2003).

* cited by examiner

AXIAL LENGTH MEASUREMENT MONITOR

RELATED APPLICATIONS

This application is a continuation of U.S. patent application Ser. No. 17/647,585, filed Jan. 10, 2022, now U.S. Pat. No. 11,497,396, issued Nov. 15, 2022, which application claims the benefit under 35 U.S.C. § 119(e) of U.S. Provisional Application No. 63/200,718, filed Mar. 24, 2021, the disclosures of which are incorporated, in their entirety, by this reference.

The subject matter of the present application is related to PCT/US2019/038270, filed on Jun. 20, 2019, published as WO 2019/246412 A1 on Dec. 26, 2019, the disclosure of which is incorporated, in its entirety, by this reference.

BACKGROUND

Recently developed light therapies have been proposed for decreasing and possibly reversing increases in axial length of the eye. It would be helpful to have improved methods and apparatus to measuring refractive error in order to determine appropriate therapies to treat the progression of refractive error such as myopia.

The prior approaches to measuring refractive error can be less than ideal. Although cycloplegia can be used to freeze the accommodative response in an effort to provide a more reliable measure of refractive error, many patients do not like to be dilated which can make daily measurements with cycloplegic an unrealistic goal. Also, subjective refraction is based on visual acuity can be less than ideal because the lens of the eye can accommodate which decreases the accuracy and repeatability of manifest refractions. While objective refraction measurements from devices such as autorefractors can automatically find the hyperfocal correction, midway between the plus and minus sides of the depth of field, these devices are susceptible to patient accommodation and can provide less than ideal results.

Although it has been proposed to measure changes in axial length to determine changes to the refractive error of the eye, the prior approaches to measuring axial length can be less than ideal in at least some respects. Some prior approaches to measuring axial length can rely on optical coherence tomography systems that are more complex than would be ideal. Also, at least some of the prior approaches to measuring axial length can rely on a difference in distance between the cornea and a single point on the retina. Work in relation to the present disclosure suggests that the retina can be less smooth than would be ideal, which can result in less than ideal results. At least some prior studies have shown that the correlation between changes in axial length and refractive error is only reasonably good when a large population of subjects (e.g. 50 to 100 subjects) are tested regularly over a period of 6 to 12 months. Consequently, changes in axial length of a particular child with a prior axial length monitor may less than ideally correlate with myopia progression, and may not be well suited for monitoring myopia progression and adjusting treatment.

Work in relation to the present disclosure suggest that prior approaches to measuring axial length may measure an approximately 50 micron zone at the fovea, and that retinal thickness can vary substantially (e.g. by approximately 50 microns or more) when measured over such a small zone, both on the same subject, and also on a population of subjects with similar ocular biometry.

In light of the above, improved methods and apparatus are needed to determine changes in refractive error and axial length of the eye.

SUMMARY

The presently disclosed methods and systems provide improved measurements of the axial length of the eye. In some embodiments, an area of the retina is measured to provide a more accurate axial length measurement. The area of the retina may comprise a maximum dimension across, e.g. a diameter, within a range from about 0.05 mm to about 2.0 mm. The area can be measured with a scanned measurement beam or plurality of substantially fixed measurement beams. In some embodiments, an OCT measurement device comprises a plurality of reference optical path lengths, in which a first optical path length corresponds to a first position of a cornea, and a second optical path length corresponds to a second position of the retina, in which the axial length is determined based on a difference between the first position and the second position. In some embodiments, an axial length map is generated, which can be used to determine alignment of the eye with the measurement device and can improve accuracy and repeatability of the measurements. In some embodiments, the OCT measurement device comprises a swept source vertical cavity surface emitting laser ("VCSEL").

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

Figure 1A:
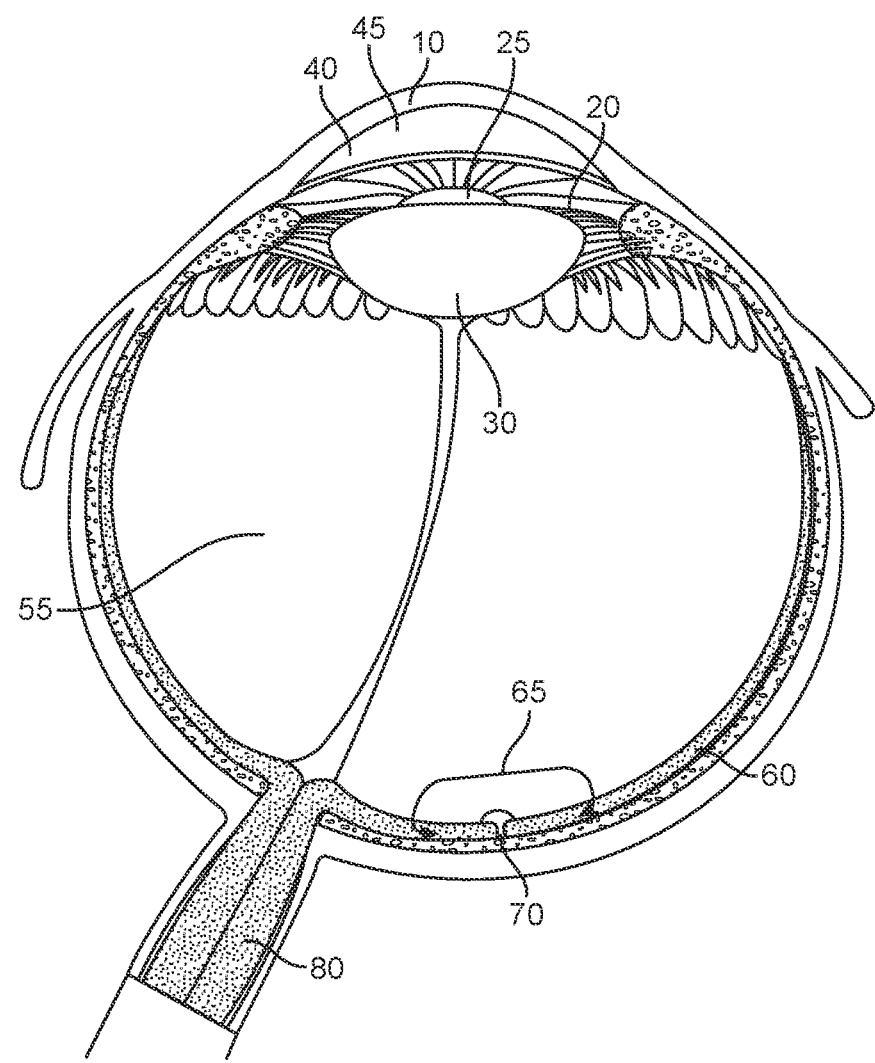
FIG. 1A shows a simplified diagram of the human eye.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein. For example, although reference is made to measuring an axial length of an eye, the methods and apparatus disclosed herein can be used to measure many types of samples, such as other tissues of the body and non-tissue material. While reference is made to generating maps of axial length, the methods and apparatus disclosed herein can be used to generate images of ocular tissue, such as cross sectional or tomographic images of an eye, such as images of one or more of the retina, the cornea, or the lens.

In some embodiments, the term axial length refers to the distance between the corneal apex to the retinal pigment epithelium (RPE) of the eye. Measurement of axial length along the optical axis of the eye can be used in order to determine paraxial focal length and optical power of refractive devices that may be provided to bring the eye to emmetropia, that is move the best focused image to the surface of the retinal pigment epithelium. Axial length can also be measured along any other suitable direction, and may be expressed as a mean value that is an average of measurements of axial length along a plurality of directions from the RPE to the corneal apex comprising the foveola, the fovea or even the entire macula. Also, in some embodiments, the axial length can be determined at least in part based on curvature of the cornea, for example where a plurality of axial lengths is determined along an annular region of the cornea and a corresponding annular region of the macula.

The presently disclosed methods, systems and devices are well suited for measuring an axial length of the eye. Work in relation to the present disclosure suggests that axial length can be used for measuring changes in eye length caused by scleral remodeling, and eye models have been developed to convert axial length into refractive error. In some embodiments, the eye models are configured to include the anterior and posterior curvatures of the cornea, the corresponding cornea thickness, as well as the location and power of the crystalline lens of the eye. In some embodiments, the power of the crystalline lens is substantially constant, and variations of anterior chamber depth can be assumed based on the eye model or measured directly. The eye model can be converted into a regression curve and included as an algorithm in an application.

The presently disclosed methods, systems and devices are well suited for combination with PCT/US2019/038270, filed on Jun. 20, 2019, entitled "MINIATURIZED MOBILE, LOW COST OPTICAL COHERENCE TOMOGRAPHY SYSTEM FOR HOME BASED OPHTHALMIC APPLICATIONS", published as WO/2019/246412, the entire disclosure of which has been incorporated by reference, and which is well suited for modification in accordance with the present disclosure. Such a system can be modified in accordance to measure axial length by modifying the ray path to measure changes in OPD of up to +/−3 mm (e.g., 21+/−3 mm).

Measurement of axial length may be carried out over a zone on the retinal surface that may have a diameter of 0.05 to 2.0 mm, preferably 0.10 to 1.5 mm. In some optical designs, a scanning system utilizing for example a movable mirror may be deployed, performing a plurality of A scans. A mean axial length may be computed from these individual measurements. Alternatively or in combination, a plurality of substantially fixed beams can be used to measure the axial length.

In some embodiments, the axial length measurement device is configured for monitoring myopia progression. Work in relation to the present disclosure suggests that myopia progression takes place substantially by deepening the vitreous compartment, although sometimes changes in corneal curvatures may also make a moderate contribution. Work in relation to the present disclosure also suggests that axial length correlates strongly with myopia progression in children, and the presently disclosed methods and apparatus are well suited for monitoring myopia progression in children.

In some embodiments, the OCT device comprises an axial length monitor with an accuracy of +/−25 microns, a resolution of 10 microns and a repeatability of +/−15 microns.

In some embodiments, the OCT device is configured to measure a change in spherocylindrical equivalent of +/−0.07D and detect a change of 0.03D, based on relationships between axial length and refraction as described herein. In some embodiments, this performance enables the device to monitor changes in refraction on a monthly basis in children, such as Asian children, whose myopia progression rate can be about 0.9D/year, on average.

In some embodiments, the OCT axial length measurement device is able to detect efficacy of myopia inhibition therapies rapidly, so that a change in therapy can be made before myopia in the patient approaches the level of high myopia (>−5D), and in many embodiments, much lower levels of myopia, such as not more than 1.0D of myopia, e.g. a refraction of −1.0D.

In some embodiments, the OCT AL measurement device comprises one or more of the following features as shown in Table 1.

TABLE 1

Features of OCT AL measurement device.

Durable, compact size
7.5 cm diameter × 25 cm length
Weight < 750 g
Passes all safety, shipping and durability testing required by EU
Accuracy of +/−25 microns, a resolution of 10 microns and a repeatability of +/−15 microns
Recharged from a laptop or charger
Data downloaded to smart device with user App through API
Data can then be uploaded into a cloud-based database
Low cost enables broad distribution, increasing accessibility
Portable and easy for children to handle and use
Ensures reliable, actionable information
Data accessible 24/7 from anywhere and can be integrated with other databases
Ai-enhanced data mining and analytics In some embodiments, the OCT AL measurement device comprises a monocular configuration, in which axial length is measured from corneal apex to the retinal pigment epithelial (RPE) layer, the patient is capable of fixating, and auto alignment or self-alignment based on visual cues.

The presently disclosed systems, devices and methods are well suited for incorporation with prior OCT approaches. The OCT interferometer may comprise one or more of a time domain OCT interferometer, a swept source OCT interferometer, spectral domain OCT interferometer or a multiple reflectance OCT interferometer. Although reference is made to a swept source VCSEL with a limited range of sweeping and the use of a plurality of VCSELs, the light source may comprise any suitable light source such as a MEMS tunable VCSEL capable of sweeping over a range of wavelengths from about 20 nm to about 100 nm or more. Although reference is made to axial length maps, in some embodiments, the OCT measurement systems and apparatus are configured to generate 3D tomographic images of the cornea and retina. In some embodiments, the 3D tomographic images of the retina comprise high resolution images of the retina, with a spatial resolution along the OCT measurement beam within a range from 4 to 25 microns, for example with resolution within a range from 2 to 10 microns.

The presently disclosed systems and methods can be configured in many ways. In some embodiments, the OCT system comprises a binocular device, in which one eye is measured and the other eye is presented with a stimulus such as a fixation stimulus. Alternatively, the OCT system may comprise a monocular device, in which one eye is measured at a time and only the measured eye is presented with a fixation stimulus, although the fellow eye may be covered with an occluder, for example.

The compact OCT system disclosed herein is well-suited for use with many prior clinical tests, such as axial length measurements. In some cases, the OCT system is used by the patient, or by a health care provider. In many instances the patient can align himself with the system, although another user can align the patient with the system and take the measurement. In some embodiments, the OCT system is integrated with prior software and systems to provide additional information to healthcare providers and can provide alerts in response to changes in axial length. The alerts are optionally sent to the patient, caregiver, and health care providers when corrective action should be taken such as a change in ocular therapy, vision stimulation therapy, medication, dosage, or a reminder to take medication.

As used herein, the "term axial length" ("AL"), refers to an axial distance of the eye from the cornea of the eye to the retina of the eye. In some embodiments, the AL is measured as a distance from the anterior surface of the cornea to the retinal pigment epithelium ("RPE").

As used herein, the term "corneal thickness" ("CT") refers to a thickness of the cornea between an anterior most corneal layer, e.g. the tear film, and a posterior most layer, e.g. the corneal endothelium.

As used herein, the term "retinal thickness" ("RT") refers to a thickness of the retina between layers used to evaluate the thickness of a retina of a patient. The RT may correspond to a thickness of the retina between an anterior surface of the retina and external limiting membrane, for example.

As used herein, the term "retinal layer thickness" ("RLT") refers to the thickness of one or more optically detectable layers of the retina. The optically detectable layers of the retina may comprise a thickness of the retina extending between the external limiting membrane and the retinal pigment epithelium, for example.

FIG. 1A shows a simplified diagram of the human eye. Light enters the eye through the cornea 10. The iris 20 controls the amount of light allowed to pass by varying the size of the pupil 25 that allows light to proceed to the lens 30. The anterior chamber 40 contains aqueous humor 45 which determines the intraocular pressure (IOP). The lens 30 focuses light for imaging. The focal properties of the lens are controlled by muscles which reshape the lens. Focused light passes through the vitreous chamber, which is filled with vitreous humor 55. The vitreous humor maintains the overall shape and structure of the eye. Light then falls upon the retina 60, which has photosensitive regions. In particular, the macula 65 is the area of the retina responsible for receiving light in the center of the visual plane. Within the macula, the fovea 70 is the area of the retina most sensitive to light. Light falling on the retina generates electrical signals which are passed to the optic nerve 80 and then to the brain for processing.

Several disorders give rise to reduced optical performance of the eye. In some cases, the axial length of the eye is undesirably long, which is related to myopia of the patient. In some cases, the intraocular pressure (IOP) is either too high or too low. This is caused, for instance, by too high or too low of a production rate of aqueous humor in the anterior chamber or drainage of aqueous humor from the anterior chamber, for example. In other cases, the retina is too thin or too thick. This arises, for instance, due to the buildup of fluid in the retina. Diseases related to an abnormal retinal thickness (RT) include glaucoma, macular degeneration, diabetic retinopathy, macular edema and diabetic macular edema, for example. In some cases, a healthy range of RT is from 175 thick to 225 μm thick. In general, abnormalities in either the TOP or the RT or both are indicative of the possible presence of one of several ophthalmological diseases. Additionally, the TOP or the RT vary in response to ophthalmological treatments or other procedures. Therefore, it is desirable to have a means to measure the TOP and/or RT for diagnosis of ophthalmological diseases and to assess the effectiveness of treatments for a given patient. In some cases, it is desirable to measure the thickness of one or more retinal layers, for example the thickness of a plurality of layers. In addition, it is desirable to process data obtained from an OCT system to assist in identifying fluid pockets or regions in the eye, as these may indicate a change in eye health.

The systems and methods disclosed herein relate to the use of optical coherence tomography (OCT) to measure the AL at multiple points in time. For instance, a patient measures their AL at multiple time points to track the progression of an ophthalmological disease such as myopia over time. As another example, a patient measures their AL at multiple time points to track their response to a photo-stimulation therapy or other treatment. In some cases, the system produces an alert when one or more recent measurements of the AL deviate significantly from previous measurements. In some cases, the system alerts the patient or the patient's physician of the change. In some instances, this information is be used to schedule a follow-up appointment between the patient and physician to, for instance, attempt a treatment of an ophthalmological condition, discontinue a prescribed treatment, or conduct additional testing.

Figure 1B:
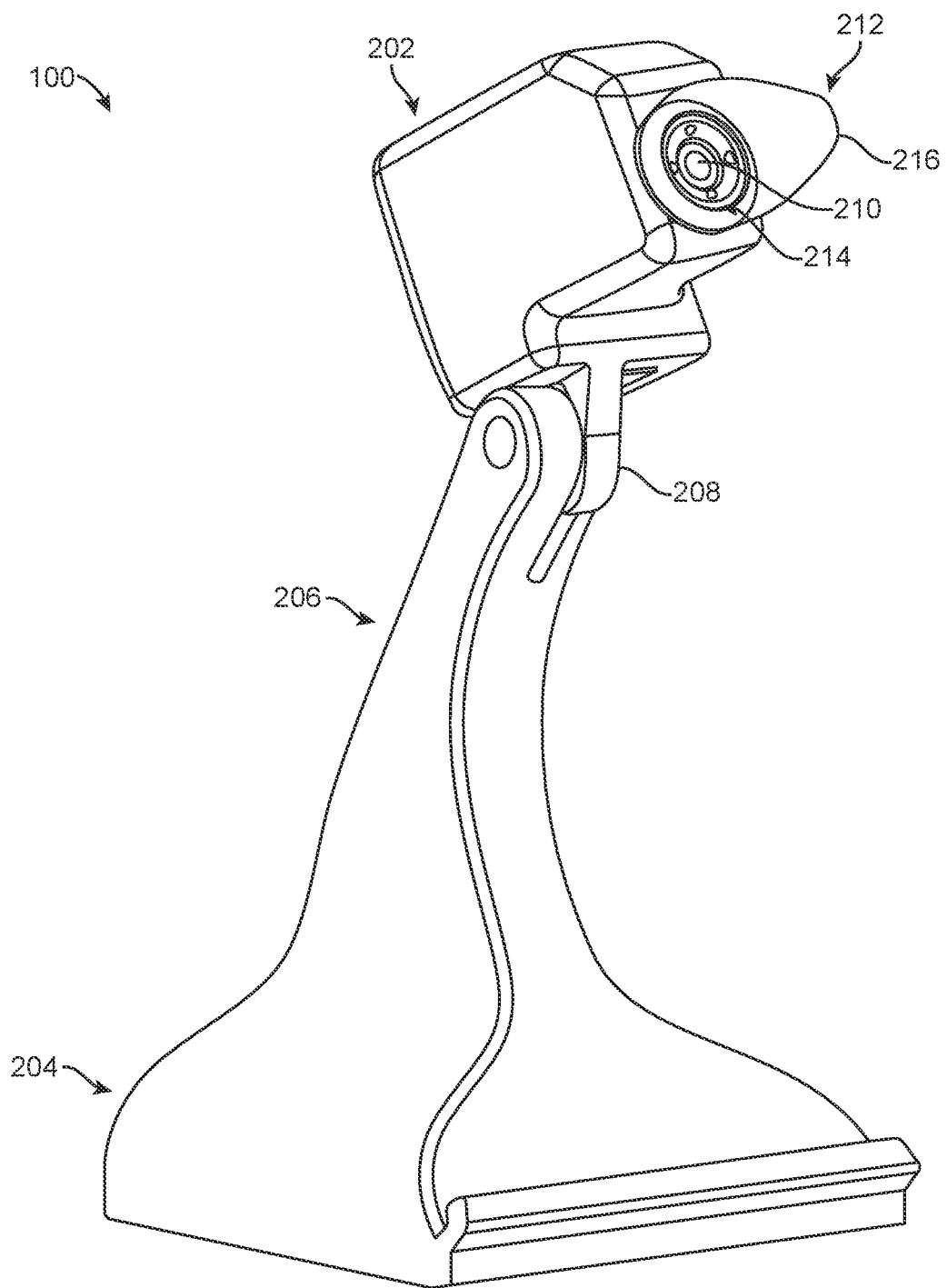
FIG. 1B shows a perspective view of a monocular optical coherence tomography (OCT) device for measuring eyes of a user, in accordance with some embodiments.

FIG. 1B shows a perspective view of a monocular optical coherence tomography (OCT) device 100 for measuring eyes of a user, in accordance with some embodiments. The OCT device 100 includes a head 202, a base 204, and a neck 206 therebetween. The head 202 is connected to the neck 206 by a coupling 208 that allows articulation of the head 202 in some embodiments. The head may be covered with a housing that encloses optical modules, scanning modules, and other related circuitry and modules to allow the OCT device 100 to measure eyes of a user, one eye at a time.

In some embodiments, the head 202 further includes a lens 210, an eyecup 212, and one or more LED lights 214. The lens 210 may be configured to direct one or more light sources from within the head 202 to focus on the retina of an eye. The eyecup 212 may be configured to locate the head of a patient, and thereby locate an eye of a patient for scanning and testing. The eyecup 212 may be rotatable, so that a protruding portion 216 may be located adjacent to an eye of a patient and extend along the side of the head (e.g., adjacent the patient's temple) when the patient's head is properly oriented to the OCT device 100. The eyecup 212 may be coupled to a sensor configured to detect the rotational orientation of the eyecup 212. In some embodiments, the OCT device 100 is configured to detect the rotational orientation of the eyecup 212 and thereby determine whether the patient has presented her right eye or left eye for scanning and measuring. More particularly, in some embodiments, the protruding portion 216 of the eyecup 212 may extend to be adjacent to either the right temple or the left temple of a patient, and thereby determine which eye of the patient is being measured. In some embodiments, eyecup 212 comprises a patient support. The patient support may comprise a headrest or a chinrest, either alternatively or in combination with the eyecup 212.

In some embodiments, a coupling 208 connects the head 202 to the neck 206 and allows a pivotal movement about the coupling. The coupling 208 may be any suitable coupling, which may be rigid, articulating, rotational, or pivotal according to embodiments. In some instances, the coupling includes a threaded fastener and a threaded nut to tighten the head against the neck in a desired orientation. The threaded nut may be operable by hand, and may comprise a knurled knob, a wing nut, a star nut, or some other type of manually operated tightening mechanism. The coupling may alternatively or additionally comprise any suitable member that allows adjustment of the angle of the head relative to the neck, and may include a cam, a lever, a detent, and may alternatively or additionally include friction increasing structures, such as roughened surfaces, peaks and valleys, surface textures, and the like.

Figure 2:
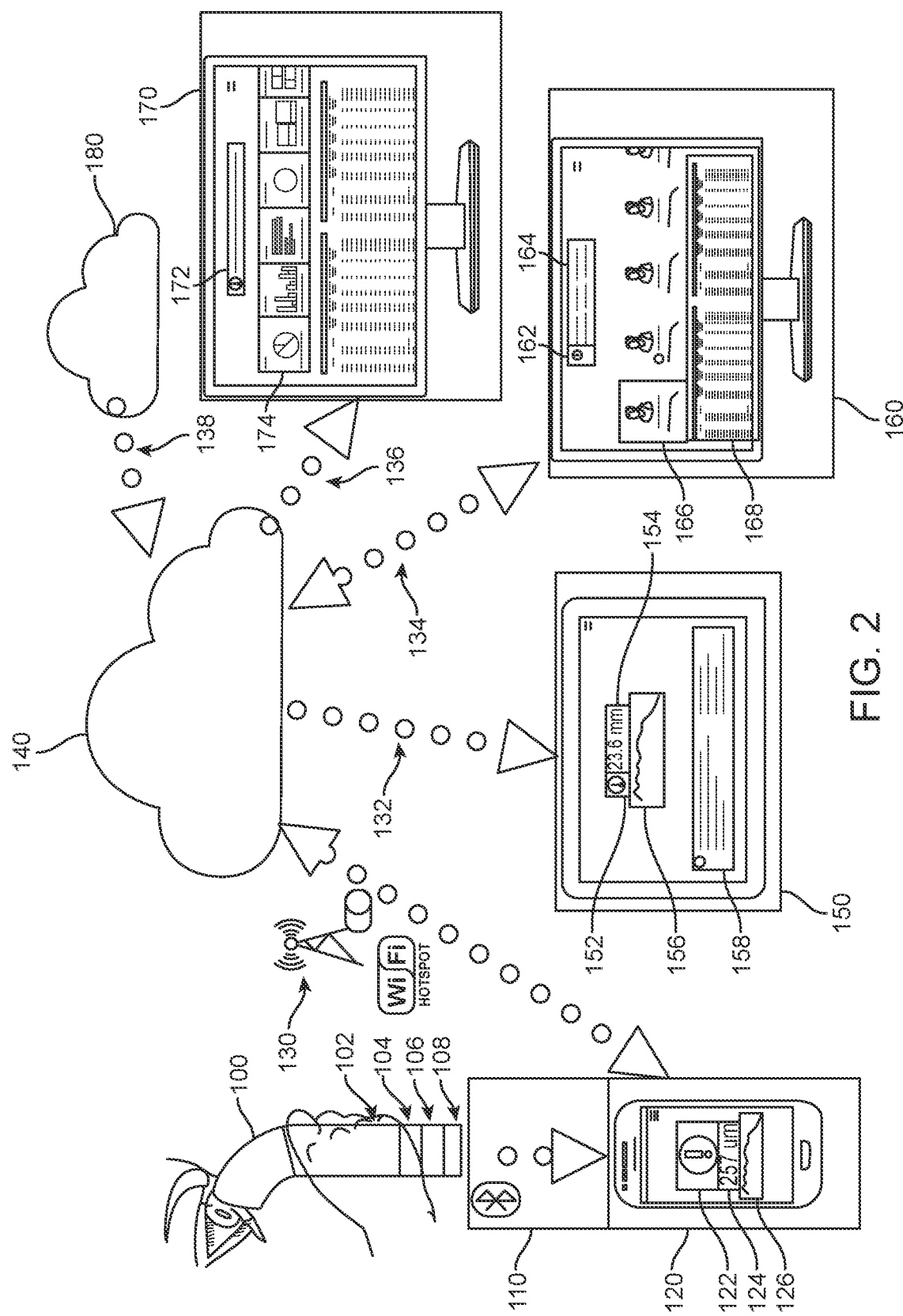
FIG. 2 shows a schematic of a system allowing a patient to measure axial length at multiple time points and to communicate the results, in accordance with some embodiments.

FIG. 2 shows a schematic of a system allowing a patient to measure the AL at multiple time points and to communicate the results, in accordance with some embodiments. The patient looks into a handheld OCT device 100 to obtain a measurement of the AL. In some embodiments, the handheld OCT device comprises optics 102, electronics 104 to control and communicate with the optics, a battery 106, and a transmitter 108. In some instances, the transmitter is a wired transmitter. In some cases, the transmitter is a wireless transmitter. In some cases, the handheld OCT device 100 communicates the results via a wireless communication channel 110 to a mobile patient device 120 such as the patient's smartphone or other portable electronic device. In some cases, the wireless communication is via Bluetooth communication. In some embodiments, the wireless communication is via Wi-Fi communication. In other embodiments, the wireless communication is via any other wireless communication known to one having skill in the art. Although reference is made to wireless communication, in some embodiments the OCT device connects by wired communication to the patient mobile device and the patient mobile device connects wirelessly to a remote server such as a cloud based server.

In some cases, the results are fully processed measurements of the AL. In some cases, all processing of the OCT data is performed on the handheld OCT device. For instance, in some embodiments, the handheld OCT device includes hardware or software elements that allow the OCT optical waveforms to be converted into electronic representations. In some cases, the handheld OCT device further includes hardware or software elements that allow processing of the electronic representations to extract, for instance, a measurement of the AL.

In some cases, the results are electronic representations of the raw optical waveforms obtained from the OCT measurement. For instance, in some embodiments, the handheld OCT device includes hardware or software elements that allow the OCT optical waveforms to be converted into electronic representations. In some cases, these electronic representations are then passed to the mobile patient device for further processing to extract, for instance, a measurement of the RT.

In some cases, the patient receives results and analysis of the AL measurement on the patient mobile app. In some embodiments, the results include an alert 122 alerting the patient that the results of the measurement fall outside of a normal or healthy range. In some cases, the results also include a display of the measured value 124. For instance, in some cases a measurement of the AL produces a result with a specific value in millimeters ("mm"), e.g. 23.6 mm. In some instances, this result corresponds to a change in axial length outside a desired range. This causes the system to produce an alert and to display the measured value on the patient mobile app. In some embodiments, the alert is transmitted to a healthcare provider, such as a treating physician. In some embodiments, the results also include a chart 126 showing a history of the patient's AL over multiple points in time.

In some instances, the patient mobile device communicates the results of the measurement via a communication means 130 to a cloud-based or other network-based storage and communications system 140. In some embodiments, the communication means is a wired communication means. In some embodiments, the communication means is a wireless communication means. In some cases, the wireless communication is via Wi-Fi communication. In other cases, the wireless communication is via a cellular network. In still other cases, the wireless communication is via any other wireless communication known to one having skill in the art. In specific embodiments, the wireless communication means is configured to allow transmission to or reception from the cloud-based or other network-based storage and communications system.

Once stored in the cloud, the results are then transmitted to other devices, in specific embodiments. In some cases, the results are transmitted via a first communication channel 132 to a patient device 150 on the patient's computer, tablet, or other electronic device. In some embodiments, the results are transmitted via a second communication channel 134 to a physician device 160 on the patient's physician's computer, tablet, or other electronic device. In some instances, the results are transmitted via a third communication channel 136 to an analytics device 170 on another user's computer, tablet, or other electronic device. In some embodiments, the results are transmitted via a fourth communication channel 138 to a patient administration system or hospital administration system 180. In some cases, each of the devices has appropriate software instructions to perform the associated function(s) as described herein.

In specific embodiments, the first communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is via any other wired or wireless communication channel or method known to one having skill in the art. In some embodiments, the first communication channel is configured to allow transmission to or reception from the cloud-based or other network-based storage and communications system. In some cases, the first communication channel is configured to only allow reception from the cloud-based or other network-based storage and communications system.

In some cases, the second communication channel is a wired communication channel or a wireless communication channel. In some instances, the communication is via Ethernet. In specific embodiments, the communication is via a local area network (LAN) or wide area network (WAN). In other embodiments, the communication is via Wi-Fi. In still other embodiments, the communication is via any other wired or wireless communication channel or method known to one having skill in the art. In some cases, the second communication channel is configured to allow transmission to or reception from the cloud-based or other network-based storage and communications system. In some embodiments, the second communication channel is configured to only allow reception from the cloud-based or other network-based storage and communications system.

In specific cases, the third communication channel is a wired communication channel or a wireless communication channel. In some instances, the communication is via Ethernet. In other instances, the communication is via a local area network (LAN) or wide area network (WAN). In still other instances, the communication is via Wi-Fi. In yet other instances, the communication is via any other wired or wireless communication channel or method known to one having skill in the art. In some embodiments, the third communication channel is configured to allow transmission to or reception from the cloud-based or other network-based storage and communications system. In some cases, the third communication channel is configured to only allow reception from the cloud-based or other network-based storage and communications system.

In some embodiments, the fourth communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is any other wired or wireless communication channel or method known to one having skill in the art. In some instances, the fourth communication channel is configured to allow transmission to or reception from the cloud-based or other network-based storage and communications system. In other cases, the fourth communication channel is configured to only allow reception from the cloud-based or other network-based storage and communications system.

A determination of the AL can be performed at many locations. For instance, a determination of the AL may be performed on the handheld OCT device. In some cases, a determination of the AL is performed at a location near to the handheld OCT device, such as by a smartphone or other portable electronic device. In some embodiments, a determination of the AL is performed on the cloud-based storage and communications system. In some instances, the handheld OCT device is configured to compress measurement data and transmit the compressed measurement data to the cloud-based storage and communications system. Alternatively or in combination, other components of the OCT system, such as a mobile device operatively coupled to the OCT device, can be configured to compress the measurement data and transmit the compressed measurement data to the cloud-based storage and communication system, for example.

In some embodiments, the patient receives results and analysis of the AL measurement on the patient device 150. In some instances, the results include an alert 152 alerting the patient that the results of the measurement fall outside of a normal or healthy range. In some cases, the results also include a display of the measured value 154. For instance, in some cases, a measurement of the AL produces a result of 23.6 mm. This result may correspond to an increase in axial length indicating an increase in myopia. In some cases, this causes the system to produce an alert and to display the measured value of 23.6 mm on the patient device. In specific cases, the results also include a chart 156 showing a history of the patient's AL over multiple points in time. In some cases, the patient device also displays instructions 158 for the patient to follow. In some instances, the instructions instruct the patient to visit their physician. In some embodiments, the instructions include the patient's name, date of most recent AL measurement, and next scheduled visit to their physician, for example.

In some embodiments, the patient's physician receives the results and analysis of the AL measurement on the physician device 160. In some instances, the results include an alert 162 alerting the physician that the results of the measurement correspond to a potentially significant change from baseline. In some cases, the results also include an alert 164 informing the physician of the patient's measurement. In some embodiments, the alert includes a suggestion that the physician call the patient to schedule an appointment or to provide medical assistance. In some embodiments, the results also include a display 166 showing the most recent measurements and historical measurements for each of the physician's patients. For instance, in some instances, a measurement of the AL produces a result of 23.6 µm. This result corresponds to a change from a baseline value indicating a possible progression of myopia. In some cases, this causes the system to produce an alert and to display the measured value of 23.6 mm on the physician app, or an amount of increase in axial length from a prior measurement. In specific cases, the physician device also displays contact and historical information 168 for each of the physician's patients.

In some embodiments, the other user receives results and analysis of the AL measurement on the analytics device 170. In some instances, the other user is a researcher investigating the efficacy of a new form of treatment. In other cases, the other user is an auditor monitoring the outcomes of a particular physician or care facility. To protect the patient's privacy, in some cases the analytics device is restricted to receive only a subset of a given patient's information. For instance, the subset is restricted so as not to include any personally identifying information about a given patient. In some cases, the results include an alert 172 alerting or indicating that a large number of abnormal or undesirable measurements have been obtained in a specific period of time. In some cases, the results include one or more graphical representations 174 of the measurements across a population of patients.

In some cases, the results and analysis on the analytics device comprise disease information such as a physician-confirmed diagnosis. In some cases, the results and analysis comprise anonymized patient data such as age, gender, genetic information, information about the patient's environment, smoking history, other diseases suffered by the patient, etc. In some cases, the results and analysis comprise anonymized treatment plans for the patient, such as a list of light therapies, prescribed medications, treatment history, etc. In some cases, the results and analysis comprise measurement results, such as the results of an AL measurement, patient refraction (eyeglass prescription), a visual function test, or the patient's compliance with a course of treatment. In some cases, the results and analysis comprise data from an electronic medical record. In some cases, the results and analysis comprise diagnostic information from visits to a patient's medical provider, such as the results of an axial length OCT scan acquired by the patient's medical provider.

In some embodiments, the patient's clinical, hospital, or other health provider receives results and analysis of the AL measurement on the patient administration system or hospital administration system 180. In some cases, this system contains the patient's electronic medical record. In some cases, the results and analysis provide the patient's health provider with data allowing the provider to update the treatment plan for the patient. In some instances, the results and analysis allow the provider to decide to call the patient in for an early office visit. In some instances, the results and analysis allow the provider to decide to postpone an office visit.

In some embodiments, one or more of the patient device, physician device, and analytics device includes a software application comprising instructions to perform the functions of the patient device, physician device, or analytics device, respectively, as described herein.

Figure 3A:
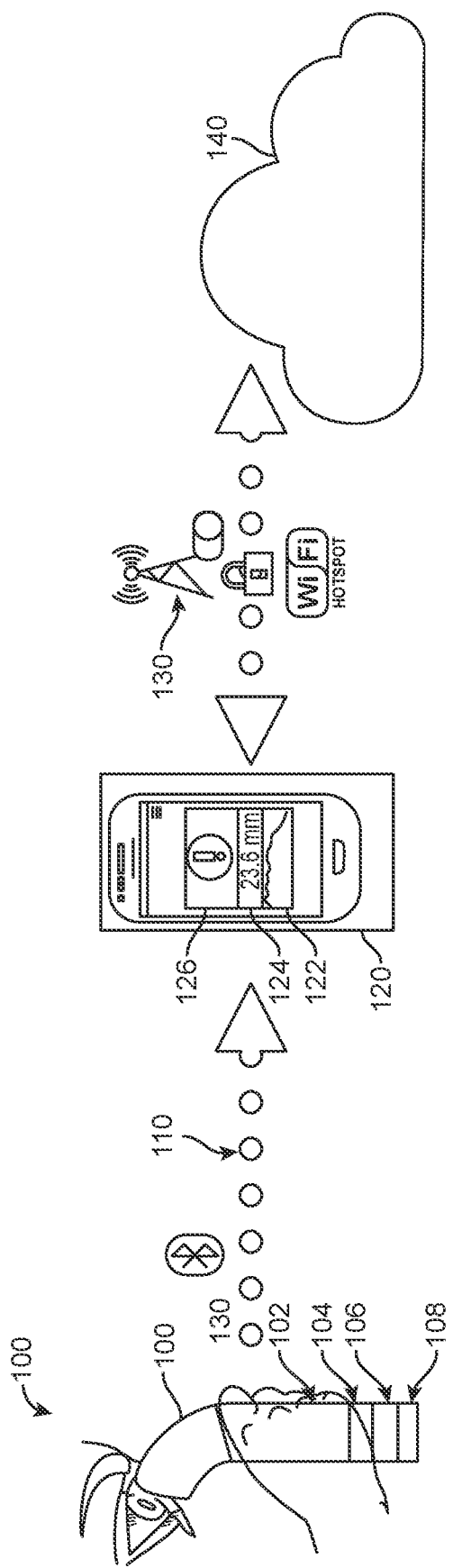
FIG. 3A shows a handheld optical coherence tomography device utilizing Bluetooth communication, in accordance with some embodiments.

FIG. 3A shows a handheld OCT device utilizing short-range wireless communication, in accordance with some embodiments. In some embodiments, the handheld OCT device 100 comprises optics 102, electronics to control and communicate with the optics 104, a battery 106, and a wireless transmitter 108. In some cases, the wireless transmitter is a Bluetooth transmitter. In some instances, the results from one or more AL measurements are stored on the handheld OCT device until an authorized user, such as the patient or another person designated by the patient, opens the patient mobile device on a smartphone or other portable electronic device. Once opened, the patient mobile device application establishes wireless communication with the handheld OCT device. In some cases, the communication is via a Bluetooth wireless communication channel 110. In some instances, the handheld OCT device communicates the results via the Bluetooth channel to a mobile patient device 120 on the patient's smartphone or other portable electronic device.

In some instances, the results include an alert 122 alerting the patient that the results of the measurement fall outside of a desired range. In specific embodiments, the results also include a display of the measured value 124. For instance, a measurement of the AL produces a result of 23.6 in some cases. This result may fall outside of a desired range. In some cases, this causes the system to produce an alert and to display the measured value of 23.6 mm on the patient mobile app. In specific embodiments, the results also include a chart 126 showing a history of the patient's AL over multiple points in time.

In some cases, the patient mobile device application communicates the results of the measurement via a wireless communication means 130 to a cloud-based or other network-based storage and communications system 140. In some instances, the wireless communication is via Wi-Fi communication. In other cases, the Wi-Fi communication is via a secure Wi-Fi channel. In still other cases, the wireless communication is via a cellular network. In specific embodiments, the cellular network is a secure cellular network. In other embodiments, the transmitted information is encrypted. In some cases, the communication channel is configured to allow transmission to or reception from the cloud-based or other network-based storage and communications system. In some cases, data is stored on the smartphone or other portable electronic device until the smartphone or other portable electronic device connects to a Wi-Fi or cellular network.

In some cases, the patient mobile device application has a feature which notifies the patient, or another person designated by the patient, when too much time has elapsed since the patient mobile device application was last opened. For instance, in some cases this notification occurs because the patient has not acquired measurements of the AL as recently as required by a measuring schedule set by their physician or other healthcare provider. In other cases, the notification occurs because the handheld OCT device has been storing the results of too many measurements and needs to transmit the data to the patient's smartphone. In specific embodiments, the patient mobile device application communicates with the cloud-based or other network-based storage and communications system to display a complete set of patient data.

Figure 3B:
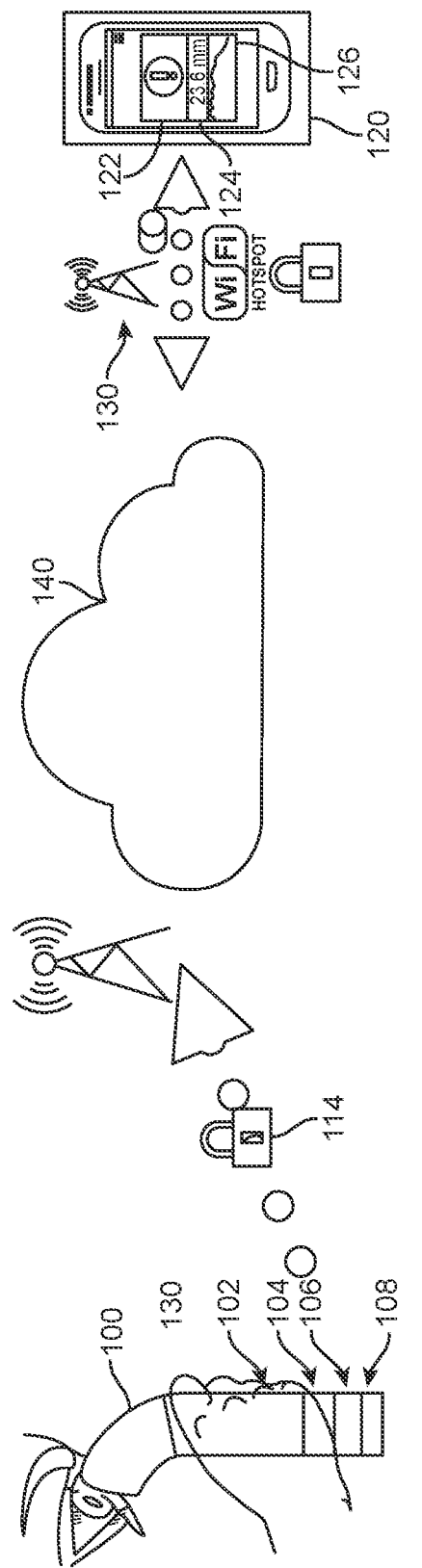
FIG. 3B shows a handheld OCT device utilizing the Global System for Mobile Communications (GSM), in accordance with some embodiments.

FIG. 3B shows a handheld OCT device capable of communicating directly with a cloud-based storage and communication system without reliance on a user device such as a smartphone, in accordance with some embodiments. In some embodiments, the handheld OCT device 100 comprises optics 102, electronics 104 to control and communicate with the optics, a battery 106, and a wireless transmitter 108. In some cases, the wireless transmitter is a GSM transmitter. In some instances, the results from one or more AL measurements are stored on the handheld OCT device. In some cases, the GSM transmitter establishes wireless communication with a cloud-based or other network-based storage and communications system 140 via a wireless communication channel 114. In specific cases, the wireless communication is via a GSM wireless communication channel. In other embodiments, the system utilizes third generation (3G) or fourth generation (4G) mobile communications standards. In such cases, the wireless communication is via a 3G or 4G communication channel.

In specific embodiments, the patient mobile device 120 receives the results of the measurement via a wireless communication means 130 from the cloud-based or other network-based storage and communications system 140. In some cases, the wireless communication is via Wi-Fi communication. In some cases, the Wi-Fi communication is via a secure Wi-Fi channel. In other cases, the wireless communication is via a cellular network. In some cases, the cellular network is a secure cellular network. In specific instances, the transmitted information is encrypted. In some embodiments, the communication channel is configured to allow transmission to or reception from the cloud-based or other network-based storage and communications system.

Once obtained from the cloud-based or other network-based storage and communications system, the results of the AL measurement are viewed in the patient mobile application, in some instances. In some cases, the results include an alert 122 alerting the patient that the results of the measurement fall outside of a normal or healthy range. In some instances, the results also include a display of the measured value 124. For instance, in some cases a measurement of the AL produces a result of 23.6 mm. This result may fall outside of a desired range as described herein. In specific embodiments, this causes the system to produce an alert and to display the measured value of 23.6 mm on the patient mobile application. In some embodiments, the results also include a chart 126 showing a history of the patient's AL over multiple points in time.

In some cases, the patient mobile device application has a feature which notifies the patient, or another person designated by the patient, when too much time has elapsed since the patient mobile device application was last opened. For instance, in some cases this notification occurs because the patient has not acquired measurements of the AL as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

In some cases, the handheld OCT device comprises both a short-range transmitter and a GSM, 3G, or 4G transmitter. In some instances, the short-range transmitter is a Bluetooth transmitter. In some cases, the handheld OCT device communicates directly with the patient mobile device application on a smartphone or other portable electronic device through the Bluetooth wireless communication channel. In some embodiments, the handheld OCT also communicates with the cloud-based or other network-based storage and communications system through the GSM, 3G, or 4G wireless communication channel. In specific cases, the cloud-based system then communicates with the patient mobile device application through a Wi-Fi, cellular, or other wireless communication channel. Alternatively, the Bluetooth transmitter is built into a docking station. In some instances, this allows for the use of older devices for patients who lack a smartphone. In some cases, the docking station also includes a means for charging the battery of the handheld OCT device.

In some cases, the handheld OCT device of FIGS. 3A and 3B is configured to be held in close proximity to the eye. For instance, in specific embodiments, the device is configured to be held in front of the eye with the detector at a distance of no more than 200 mm from the eye. In other embodiments, the devices are configured to be held in front of the eye with the detector at a distance of no more than 150 mm, no more than 100 mm, or no more than 50 mm from the eye. In specific instances, the handheld OCT devices further comprise housing to support the light source, optical elements, detector, and circuitry. In some cases, the housing is configured to be held in a hand of a user. In some cases, the user holds the devices in front of the eye to direct the light beam into the eye. In some instances, the devices include a sensor to measure which eye is being measured. For instance, in specific embodiments, the devices include an accelerometer or gyroscope to determine which eye is measured in response to an orientation of the housing. The devices optionally include an occlusion structure coupled to the housing and the sensor that determines which eye is measured. The occlusion structure occludes one eye while the other eye is measured. In some cases, the devices include a viewing target to align the light beams with a portion of the retina. For instance, in specific embodiments, the devices include a viewing target to align the light beams with a fovea of the eye. In some cases, the viewing target is a light beam. In some cases, the viewing target is a light emitting diode. In other cases, the viewing target is a vertical cavity surface emitting laser (VCSEL). In still further cases, the viewing target is any suitable viewing target as will be known to one having ordinary skill in the art.

The optical components described herein are capable of being miniaturized so as to provide the handheld OCT device with a reduced physical size and mass, as described herein, as will be appreciated by one of ordinary skill in the art.

In some embodiments, the handheld OCT devices of FIGS. 3A and 3B are small enough and light enough to be easily manipulated with one hand by a user. For instance, in some embodiments, the device has a mass within a range from about 100 grams to about 500 grams, although the device may be heavier and may comprise a mass within a range from about 500 grams to about 1000 grams, for example. In some embodiments, the device has a mass within a range from about 200 grams to about 400 grams. In some embodiments, the device has a mass within a range from about 250 grams to about 350 grams. In specific embodiments, the device has a maximum distance across within a range from about 80 mm to about 160 mm. In specific embodiments, the device has a maximum distance across within a range from about 100 mm to about 140 mm. In specific embodiments, the device has a width within a range from about 110 mm to about 130 mm. In some embodiments, the maximum distance across comprises a length. In some embodiments, the device has a width less than its length. In specific embodiments, the device has a width within a range from about 40 mm to about 80 mm. In specific embodiments, the device has a width within a range from about 50 mm to about 70 mm. In specific embodiments, the device has a width within a range from about 55 mm to about 65 mm.

Figure 4:
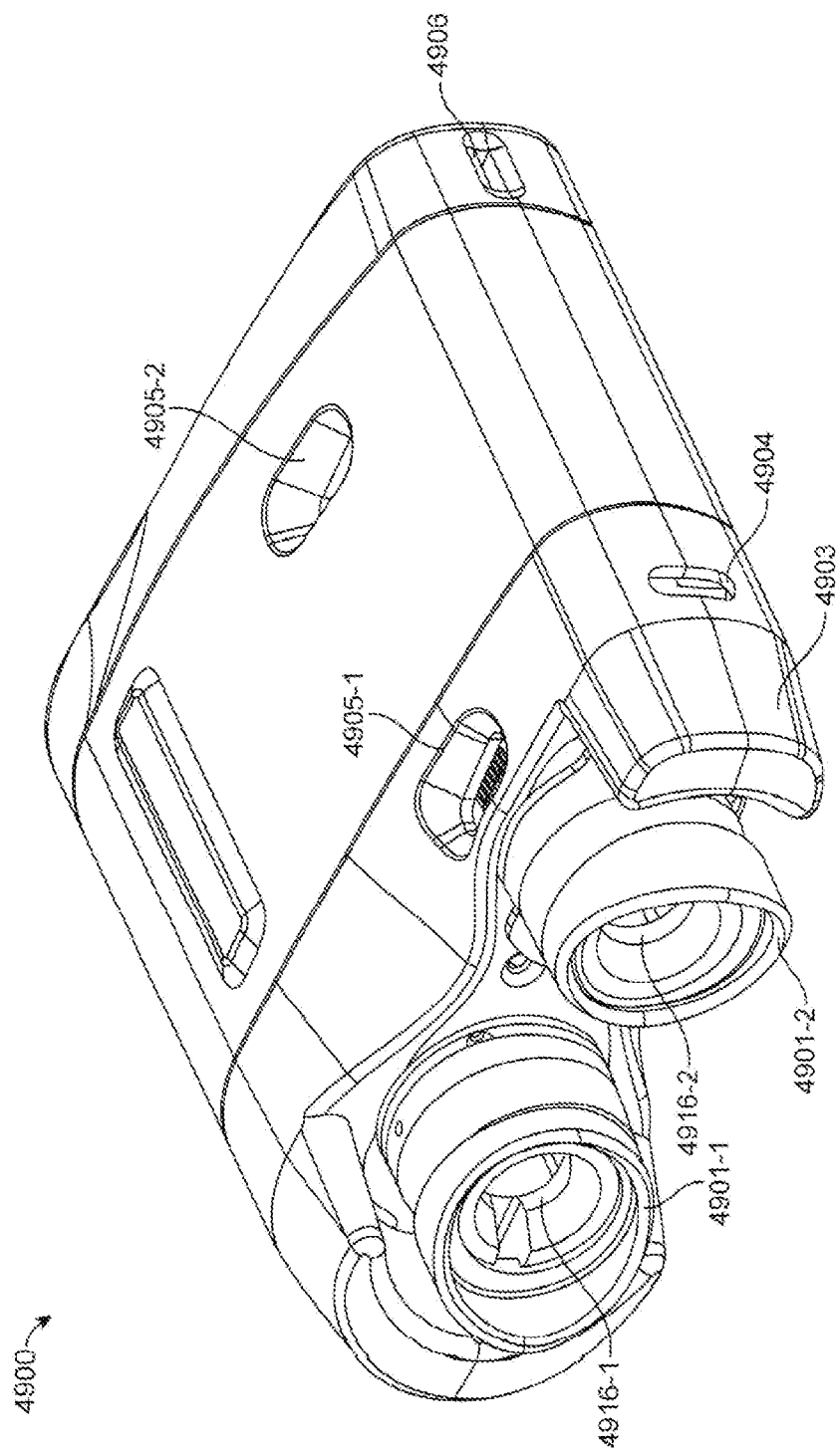
FIG. 4 shows a perspective view of a binocular OCT device for measuring eyes of a user, in accordance with some embodiments.

FIG. 4 shows a perspective view of a binocular OCT device 4900 for measuring eyes of a user, in accordance with some embodiments. The binocular OCT device 4900 comprises a first adjustable lens 4916-1 that is optically coupled to an OCT measurement system and a first fixation target configured within a handheld unit body 4903 (e.g., a housing), both of which are hidden from view in this figure. Similarly, a second adjustable lens 4916-2 may be optically coupled to the OCT measurement system and a second fixation target (hidden). The first adjustable lens 4916-1 may be part of a first free space optics that is configured to provide a fixation target and measure an axial length of the user's eye, whereas the second adjustable lens 4916-2 may be part of a second free space optics that is configured to only provide a fixation target so as to reduce a number of components in the binoculars OCT device 4900. For instance, while both free space optics provide the user with a fixation target, only one of the free space optics is used to measure the axial length as the binocular OCT device 4900 may be turned upside down, i.e. inverted, after the user measures a first eye such that the user may measure the other eye.

The binocular OCT device 4900, in this embodiment, comprises an interpupillary distance (IPD) adjustment mechanism 4905 that is accessible on the exterior of the handheld unit body 4903. In this embodiment, the IPD adjustment mechanism 4905 comprises two components, a first component 4905-1 that adjusts the distance between the lenses 4916-1 and 4916-2 to match the IPD of a user's pupils when the user places the binocular OCT device 4900 front of the user's eyes when the eye cups 4901-1 and 4901-2 rest on the user's face.

This IPD can be set by a healthcare professional and locked into position for the user to measure one or more of the AL, corneal thickness, or retinal thickness at home. Alternatively, the IPD can be user adjustable. A switch 4904 may be used to adjust the lenses 4916-1 and 4916-2 to match a user's refraction, i.e. eyeglass prescription. Alternatively, a mobile device, such as a tablet can be used program the refraction of each eye of the patient. For example, the user may fixate on the first fixation target with one eye and a second fixation target with another eye, and the movable lenses adjusted to the user's refraction. The switch 4904 may selectively adjust the assemblies of the lenses 4916-1 and 4916-2 within the handheld unit body 4903 to change the positioning of the lenses 4916-1 and 4916-2. These positions can be input into the device by a health care professional and stored in a processor along with an orientation from an orientation sensor as described herein. The device can be inverted, and the process repeated. Alternatively, or additionally, the prescription for each eye can be stored in the processor and the lenses adjusted to the appropriate refraction for each eye in response to the orientation of the orientation sensor.

Both of the components 4905-1 and 4905-5 may be implemented as one or more wheels that the health care professional manually rotates. Alternatively, the IPD adjustment mechanism 4905 may be motorized. In this regard, the components 4905-1 and 4905-5 may be configured as directional switches that actuate motors within the handheld unit body 4903 to rotate gears within the handheld unit body 4903 based on the direction in which the user directs the switch.

The switch 4904 can be used to adjust the focusing of the binocular OCT device 4900. For example, because the focal change effected by adjustment of the lenses 4916-1 and 4916-2 can be measured in a customary unit of refractive power (e.g., the Diopter) by adjustment of the lenses 4916-1 and 4916-2. The Diopter switch 4906 may also comprise a directional switch that actuates a motor within the handheld unit body 4903 to rotate gears within the handheld unit body 4903 based on the direction in which the healthcare professional directs the switch to adjust the refractive power of the binocular OCT device 4900. As the binocular OCT device 4900 may comprise an electronic device, the binocular OCT device 4900 may comprise a power switch 4906 to control powering of the binocular OCT device 4900.

Each of the eyecups 4901-1 and 4901-2 can be threadedly mounted and coupled to the housing to allow adjustment of the position of the eye during measurements. Work in relation to the present disclosure suggests that the eyecups can be adjusted by a healthcare professional and locked in place to allow sufficiently reproducible positioning of the eye for AL measurements as described herein. Alternatively, or in combination, an eye position sensor, such as a Purkinje image sensor can be used to determine a distance from the eye to the OCT measurement system.

The binocular OCT device 4900 may comprise appropriate dimensions and weight for in home measurements and for the user to take the binocular OCT system on trips. For example, the binocular OCT system may comprise a suitable length, a suitable width and a suitable height. The length can extend along an axis corresponding to the users viewing direction. The length can be within a range from about 90 mm to about 150 mm, for example about 130 mm. The width can extend laterally to the length and can be within a range from about 90 mm to about 150 mm for example about 130 mm. The height can be within a range from about 20 mm to about 50 mm, for example. In some embodiments, the length is within a range from about 110 mm to 210 mm, the width within a range from about 100 mm to 200 mm and a height within a range from about 50 mm to about 110 mm. In some embodiments, a maximum distance across the device is within a range from about 200 mm to about 350 mm, for example approximately 300 mm.

The weight of the binocular OCT system can be within a range from about 1 pound to two pounds, e.g. 0.5 kg to about 1 kg.

The binocular OCT device 4900 can be configured to be dropped and still function properly. For example, the binocular OCT device can be configured to be dropped from a height of about 30 cm and still function so as to perform AL measurements accurately, e.g. with a change in measured AL of no more than the repeatability of the measurements. The binocular OCT system can be configured to be dropped from a height of about 1 meter without presenting a safety hazard, for example from glass breaking.

Figure 5:
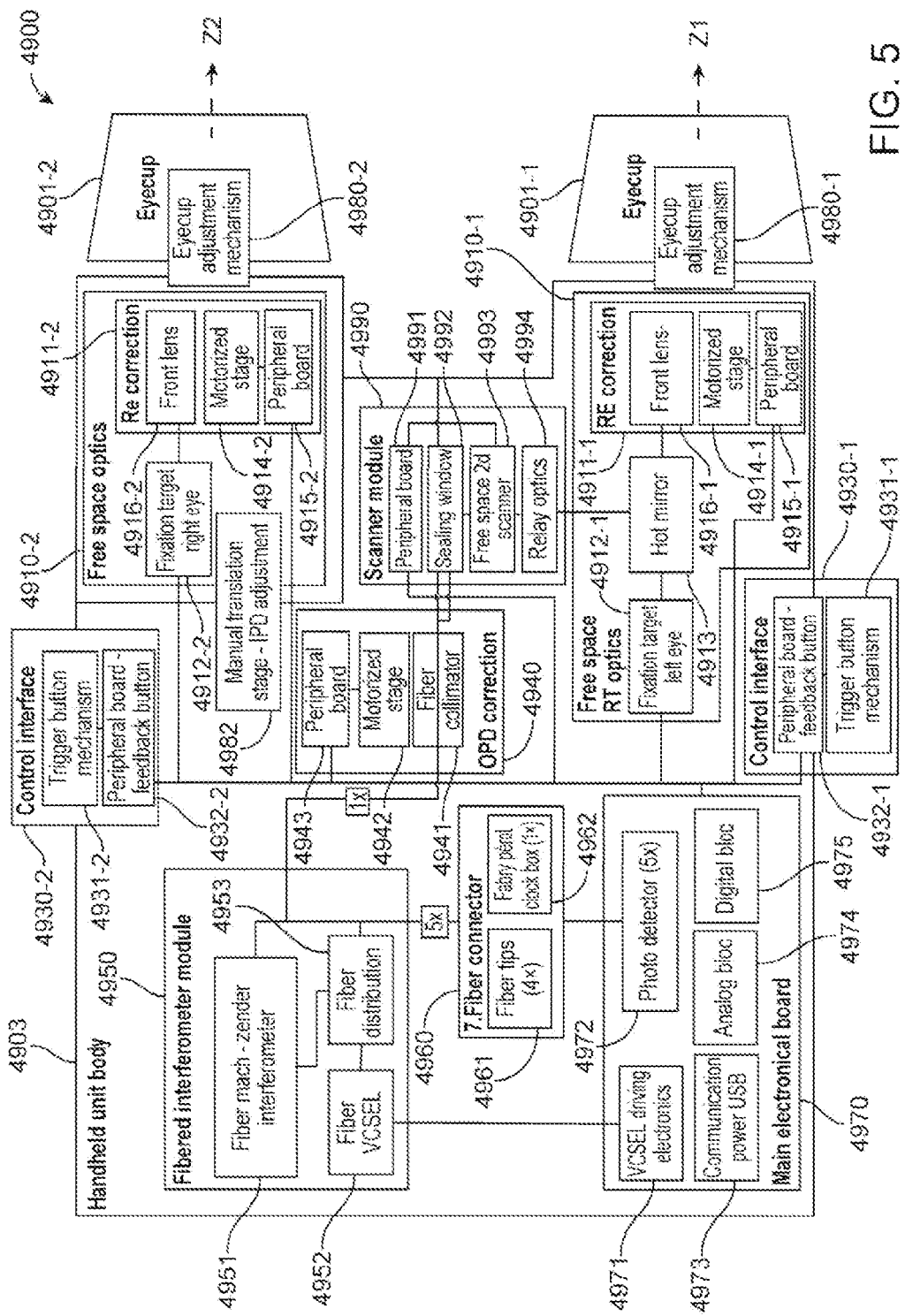
FIG. 5 shows a block diagram of the binocular OCT device illustrating various components within the handheld unit body, in accordance with some embodiments.

FIG. 5 shows a block diagram of the binocular OCT device 4900 illustrating various components within the handheld unit body 4903, in accordance with some embodiments. For instance, the binocular OCT device 4900 comprises free space optics 4910-1 and 4910-2. Each of the free space optics 4910-1 and 4910-2 comprises a fixation target 4912 for its respective eye that allows the user to fixate/gaze on the target while the user's AL is being measured, and to allow fixation with the other eye, so as to provide binocular fixation. The fixation target may comprise an aperture back illuminated with a light source such as an LED, (e.g., a circular aperture to form a disc shaped illumination target, although a cross or other suitable fixation stimulus may be used. The free space optics 4910-1 and 4910-2 may also comprise refractive error (RE) correction modules 4911-1 and 4911-2, respectively, that comprises the lenses 4916-1 and 4916-2, respectively. These lenses can be moved to preprogrammed positions corresponding to the refractive error of the appropriate eye. A peripheral board 4915-1 and 4915-2 in the free space optics modules 4910-1 and 4910-2 provides electronic control over a motorized stage 4914-1 and 4914-2, respectively to correct for the refractive error of the respective eye viewing the fixation target of the binocular OCT device 4900.

As discussed herein, the binocular OCT device 4900 may comprise eye cups 4901-1 and 4901-2 that may be used to comfortably rest the binocular OCT device 4900 on the user's face. They may also be configured to block out external light as the user gazes into the binocular OCT device 4900. The eye cups 4901 may also comprise eye cup adjustment mechanisms 4980-1 and 4980-2 that allow the health care professional and optionally the user to move the eye cups 4901-1 and 4901-2 back and forth with respect to the handheld unit body 4903 to comfortably position the eye cups on the user's face and appropriately position each eye for measurement.

In some embodiments, the binocular OCT device 4900 comprises a fibered interferometer module 4950 that comprises a single VCSEL or a plurality of VCSELs 4952. The one or more VCSELs 4952 are optically coupled to a fiber distribution module 4953, which is optically coupled to fiber Mach-Zender interferometer 4951. With embodiments comprising a plurality of VCSELs 4952, the VCSELS may each comprise a range of wavelengths different from other VCSEL 4952 in the plurality in order to extend a spectral range of light. For example, each VCSEL 4952 may pulse laser light that is swept over a range of wavelengths for some duration of time as described herein. The swept range of each VCSEL 4952 may partially overlap an adjacent swept range of another VCSEL 4952 in the plurality as described herein. Thus, the overall swept range of wavelengths of the plurality of VCSELs 4952 may be extended to a larger wavelength sweep range. Additionally, the firing of the laser light from the plurality of VCSELs 4952 may be sequential. For example, a first VCSEL of the plurality of VCSELs 4952 may sweep a laser pulse over a first wavelength for some duration. Then, a second VCSEL of the plurality of VCSELs 4952 may sweep a laser pulse over a second wavelength for some similar duration, then a third, and so on.

The laser light from the one or more VCSELs 4952 is optically transferred to the fiber distribution module 4953, where a portion of the laser light is optically transferred to a fiber connector 4960 for analysis in a main electronic board 4970. The fiber connector 4960 may connect a plurality of optical fibers from the fiber distribution module 4953 to the fiber connector module 4960. Another portion of the laser light is optically transferred to an optical path distance (OPD) correction module 4940 and ultimately to the free space optics 4910-1 for delivery to a user's eye and measurement of the user's eye with a portion of the measurement arm of the Mach-Zender interferometer. For example, the OPD correction module 4940 may comprise a peripheral board 4943 that is controlled by the main electronic board 4970 to actuate a motorized stage 4942 to change the optical path distance between the user's eye, a coupler of the Mach-Zender interferometer and the one or more VCSELs 4952. The OPD correction module 4940 may also comprise a fiber collimator 4941 that collimates the laser light from the VCSELs 4952 before delivery to the user's eye, and the fiber collimator can be translated with the OPD correction module 4940.

A controller interface 4930 may be used to receive user inputs to control the binocular OCT measurement system. The controller interface may comprise a first controller interface 4930-1 and a second controller interface 4930-2. The controller interface 4930 may comprise a trigger button mechanism that allows a user to initiate a sequence of steps to align the eye and measure the retina as described herein. Alternatively or in combination, the device may be configured with an auto-capture function, such that the data is automatically acquired when the device is aligned to the eye within appropriate tolerances.

In some embodiments, the binocular OCT device 4900 comprises a scanner module 4990 that scans the laser light from the one or more VCSELs 4952 in a pattern (e.g., a stop and go scan pattern, a star scan pattern, a continuous scan pattern, a Lissajous scan pattern, or a flower scan pattern (rose curve)). For example, a peripheral board 4991 of the scanner module 4990 may be communicatively coupled to the main electronic board 4970 to receive control signals that direct the scanner module 4990 to scan the pulsed laser light from the VCSELs 4952 in a pattern to perform an optical coherence tomography (OCT) measurement on the user's eye. The scanning module 4990 may comprise a sealing window 4992 that receives the laser light from the fiber collimator 4941 and optically transfers the laser light to a free space two-dimensional scanner 4993, which provides the scan pattern of the laser light. The two-dimensional scanner may comprise a scanner as described herein, such as a two-axis galvanometer, or a two axis electro-static scanner, for example. When present, the sealing window 4992 may be used to keep the internal components of the binocular OCT device 4900 free of dirt and/or moisture. The laser light is then optically transferred to relay optics 4994 such that the scanned laser light can be input to the user's eye via the free space RT optics 4910-1. In this regard, the scanned laser light may be transferred to a hot mirror 4913 such that infrared light may be reflected back towards the hot mirror, the scanning mirror and focused into an optical fiber tip coupled to the collimation lens. The hot mirror 4913 generally transmits visible light and reflects infrared light, and may comprise a dichroic short pass mirror, for example.

The scanner and associated optics can be configured to scan any suitably sized regions of the retina, such as regions comprising the fovea. In some embodiments and scanner and associated optics are configured to scan the cornea while the retina is scanned. In some embodiments, the scanner is configured to scan the retina with a scanning pattern, such as a predetermined scanning pattern in response to instructions stored on a processor such as the controller. For example, the scanner can be configured to scan the retina over an area comprising a maximum distance across within a range from about 0.05 to 2.0 mm, for example. The maximum distance across may comprise a diameter, and can be within a range from about 0.1 mm to about 1.5 mm. The dimensions of corneal scanning can be similar. The scanning region of the retina may comprise an area larger than maps of AL in order to account for slight errors in alignment, e.g. up to 0.5 mm in the lateral positioning of the eye in relation to the OCT system, for example in order to compensate for alignment errors, e.g. by aligning the map based on the measured position of the eye. The size of the OCT measurement beam on the retina can be within a range from about 25 microns to about 75 microns. In some embodiments, the mirror is moved with a continuous trajectory corresponding to a scan rate on the retina within a range from about 10 mm per second to about 200 mm per second, and the scan rate can be within a range from about 50 mm per second to about 200 mm per second. The displacement of the beam during an A-scan can be within a range from about 2 to 10 microns, for example. The beams for each of a plurality of A-scans can overlap. In some embodiments, the mirror moves continuously with one or more rotations corresponding to the trajectory of the scan pattern and the swept source VCSEL turns on and off with a suitable frequency in relation to the size of the beam and the velocity of the beam on the retina. In some embodiments each of the plurality of A-scans overlaps on the retina during at least a portion of the scan pattern.

In embodiments where the one or more VCSELs comprises a plurality of VCSELs, the plurality of VCSELs can be sequentially scanned for each A-scan, such that the measurement beams from each of the plurality of VCSELs overlaps on the retina with a prior scan, and the cornea may be scanned similarly. For example, each of the sequentially generated beams from each of the plurality of VCSELs from a first A-scan can overlap with each of the sequentially generated beams from each of the plurality of VCSELs from a second A-scan along the trajectory.

As described herein, the binocular OCT device 4900 may comprise an IPD adjustment via the components 4905-1 and/or 4905-2. These components may be communicatively coupled to a manual translation stage IP adjustment module 4982 that perform the actuation of the free space optics modules 4910-1 and 4910-2, so as to change a separation distance between the free space optics modules and adjust the IPD.

The main electronic board 4970 may comprise a variety of components. For example, a photodetector 4972 may be used to receive laser light directed from the VCSELs 4952 through the fiber connector 4960 as well interfering light reflected from the user's eye. The fiber connector 4960 may comprise a module 4961 that couples a plurality of optical fibers, for example four optical fibers, to a plurality of detectors, for example five detectors. The fiber connector 4960 may also comprise an interferometer clock box 4962 (e.g. an etalon) that may be used in phase wrapping light reflected back from the user's eyes, as shown and described herein. Once received by the photodetectors 4972, the photodetectors 4972 may convert the light into electronic signals to be processed on the main electronic board 4970 and/or another processing device. The plurality of photo detectors may comprise two detectors of a balanced detector pair coupled to the fiber Mach-Zender interferometer, a clock box detector, and a pair of power measurement detectors, for example.

The main electronic board 4970 may comprise a communication power module 4973 (e.g., a Universal Serial Bus, or "USB") that can communicatively couple the binocular OCT device 4900 to another processing system, provide power to the binocular OCT device 4900, and/or charge a battery of the binoculars OCT device 4900. Of course, the binocular OCT device 4900 may comprise other modules that may be used to communicate information from the binocular OCT device 4900 to another device, including for example, Wi-Fi, Bluetooth, ethernet, FireWire, etc.

The main electronic board 4970 may also comprise VCSEL driving electronics 4971 which direct how and when the VCSELs 4952 are to be fired towards the user's eyes. Other components on the main electronic board 4970 comprise an analog block 4974 and a digital block 4975 which may be used to process and/or generate analog and digital signals, respectively, being transmitted to the binocular OCT device 4900 (e.g., from an external processing system), being received from various components within the binocular OCT device 4900, and/or being received from various components within the binocular OCT device 4900. For example, the peripheral feedback button 4932 may generate an analog signal that is processed by the analog block 4974 and/or digital clock 4975, which may in turn generate a control signal that is used to stimulate the motorized stage module 4942 via the peripheral board 4943. Alternatively, or additionally, the analog block 4974 may process analog signals from the photodetectors 4972 such that they may be converted to digital signals by the digital block 4975 for subsequent digital signal processing (e.g., FFTs, phase wrapping analysis, etc.).

Figure 6:
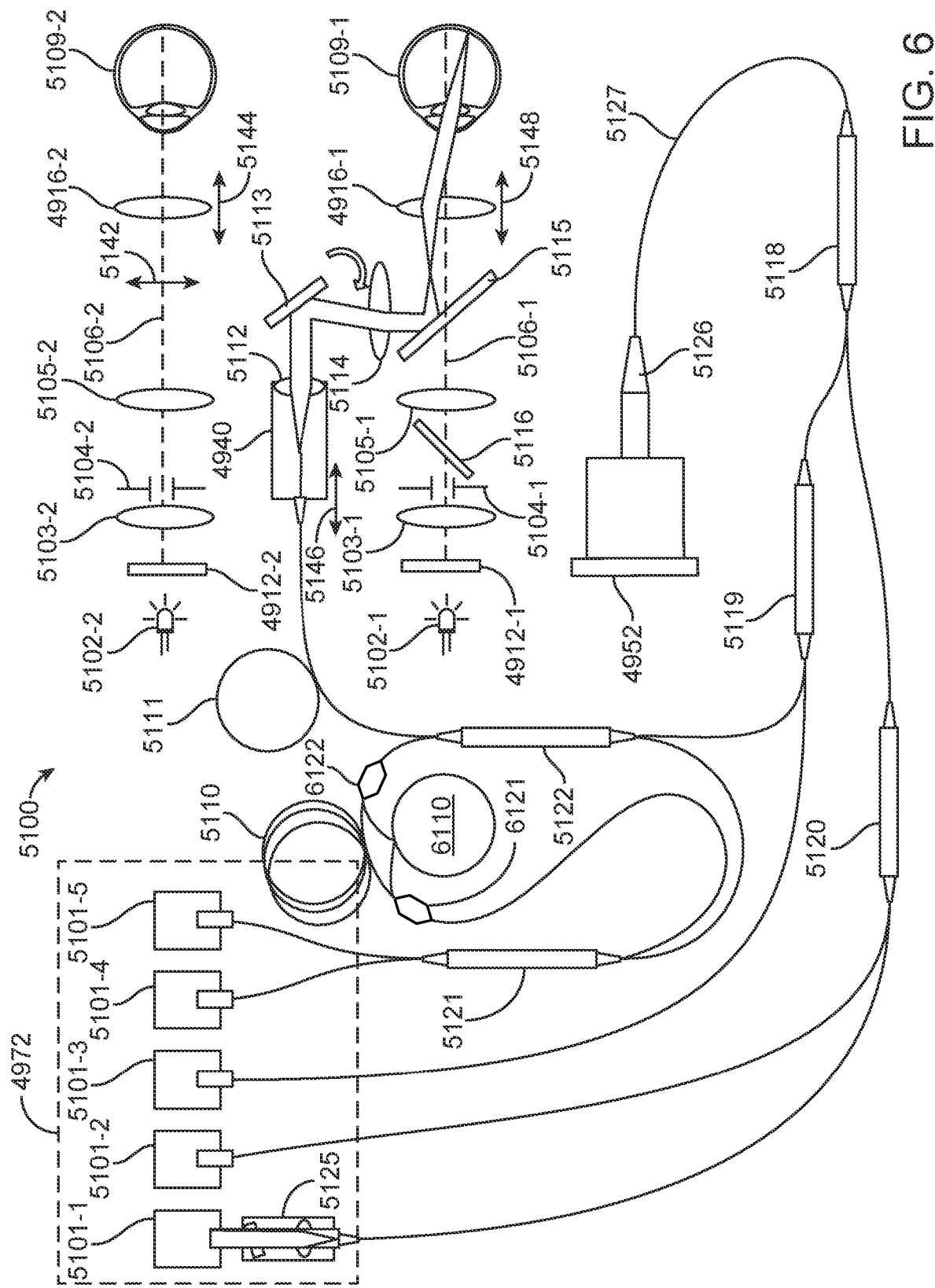
FIG. 6 shows a schematic of an optical configuration that may be implemented with the OCT binocular, in accordance with some embodiments.

FIG. 6 shows a schematic of an optical configuration 5100 that may be implemented with the OCT binocular 4900, in accordance with some embodiments. The optical configuration 5100 comprises one or more VCSELs 4952 that are fiber coupled via an optical coupler 5126. As discussed above, the one or more VCSELs 4952 may be swept over a range of wavelengths when fired. For embodiments with a plurality of VCSELs 4952, the wavelengths may partially overlap a wavelength sweep range of another VCSEL 4952 in the plurality so as to increase in overall sweep range of the VCSELs 4952. In some instances, this overall sweep range is centered around approximately 850 nm. The laser light from the one or more VCSELs 4952 is propagated through the fiber coupler 5126 to a fiber optic line 5127, where another optical coupler 5118 splits a portion of the optical energy from the one or more VCSELs 4952 along two different paths.

In the first path, approximately 95% of the optical energy is optically transferred to another optical coupler 5119 with approximately 5% of the optical energy being optically transferred to an optical coupler 5120. In the second path, the optical energy is split yet again via an optical coupler 5120. In this regard, approximately 75% of the optical energy from the optical coupler 5120 is transferred to a phase correction detector 5101-1 through an interferometer such as a Fabry Perot interferometer comprising an etalon. The etalon and detector may comprise components of an optical clock 5125. The optical clock 5125 may comprise a single etalon, for example. The etalon may comprise substantially parallel flat surfaces and be tilted with respect to a propagation direction of the laser beam. The surfaces may comprise coated or uncoated surfaces. The material may comprise any suitable light transmissive material with a suitable thickness. For example, the etalon may comprise a thickness within a range from about 0.25 mm to about 5 mm, for example within a range from about 0.5 mm to about 4 mm. The reflectance of the etalon surfaces can be within a range from about 3% to about 10%. The etalon can be tilted with respect to the laser beam propagation direction, for example tilted at an angle within a range from about 5 degrees to about 12 degrees. The finesse of the etalon can be within a range from about 0.5 to about 2.0, for example, for example within a range from about 0.5 to 1.0. The etalon may comprise any suitable material such as an optical glass. The thickness, index of refraction, reflectance and tilt angle of the etalon can be configured to provide a substantially sinusoidal optical signal at the clock box detector. The finesse within the range from about 0.5 to 2.0 can provide substantially sinusoidal detector signals that are well suited for phase compensation as described herein, although embodiments with higher finesse values can be effectively utilized.

In some embodiments, the clockbox may comprise a plurality of etalons. The approach can be helpful in embodiments wherein the one or more VCSELs comprises a plurality of VCSELs, and the plurality of etalons provides additional phase and clock signal information. For example, the clockbox may comprise a first etalon and a second etalon arranged so that light is transmitted sequentially through the first etalon and then the second etalon, e.g. a series configuration, which can provide frequency mixing of the clock box signals and decrease the number of detectors and associated circuitry used to measure phase of the swept source. Alternatively, the plurality of etalons can be arranged in a parallel configuration with a plurality of etalons coupled to a plurality of detectors.

The phase correction detector 5101-1 may use the light signals from the optical clock 5125 to correct the phase of light reflected from a user's eyes 5109-1 by matching the phases of the one or more VCSELs 4952 via phase wrapping of the light from the one or more VCSELs 4952 as described herein. The remaining 25% of the optical energy from the optical coupler 5120 may be optically transferred to a detector 5101-2 for optical safety. For instance, the detector 5101-2 may be used to determine how much optical energy is being transferred to the user's eye 5109-1 or 5109-2, depending on the orientation of the device. If the binocular OCT device 4900 determines that the detector 5101-2 is receiving too much optical energy that may damage the user's eyes, then the binocular OCT device 4900 may operate as a "kill switch" that shuts down the one or more VCSELs 4952. Alternatively, or additionally, the binocular OCT device 4900 may monitor the detector 5101-2 to increase or decrease the optical energy from the one or more VCSELs 4952 as deemed necessary for laser safety and/or signal processing. The OCT device may comprise a second safety detector 5101-3 to provide a redundant measurement for improved eye safety.

The optical energy transferred to the optical coupler 5119 (e.g., approximately 95% of the optical energy from the one or more VCSELs 4952) is also split along two paths with approximately 99% of the remaining optical energy being optically transferred along a fiber to an optical coupling element 5122 and with approximately 1% of the remaining optical energy also being optically transferred to a detector 5101-3 for laser safety of the binocular OCT device 4900. The portion of the optical energy transferred to to the optical coupler 5122 may be split by the optical coupler 5122 between two optical path loops 5110 and 5111 of the Mach-Zender interferometer, approximately 50% each, for example. The reference optical path loop 5110 may comprise a portion of the reference arm of the interferometer and provide a reference optical signal for one or more of the AL measurement, the corneal thickness measurement or the retinal thickness measurement of the user's eye 5109-1 (e.g., the measurement signal reflected from the user's retina through the measurement optical path loop 5111).

In some embodiments, the reference arm comprises a plurality of reference arms of different distances and corresponding different optical path lengths. For example, the reference optical path may comprise a plurality of optical fibers in a parallel optical configuration to provide a plurality of different optical path lengths. Although reference is made to a parallel configuration one of ordinary skill in the art will understand that this refers to the coupling arrangement of the fibers, and not necessarily to the orientation along the lengths of the fibers, which can be arranged in any suitable non-parallel configuration, e.g. with loops. In some embodiments, the reference optical path loop 5110 comprises a portion of a first reference optical path with a first reference optical path length so as measure the location of the cornea of the eye. A second reference optical path comprises a different reference length. A second reference optical path loop 6110 comprises a portion of the second reference optical path with the second reference optical path length so to measure a location of the retina of the eye. In some embodiments, the reference optical path is split into the first reference optical path with coupler 6122, which is coupled to the first reference optical path loop 5110 and the second optical path loop 6110 in order to split the reference beam into the first reference beam and the second reference beam. The first reference beam and the second reference beam may be combined with a coupler 6121 in order to combine the first reference beam and the second reference beam prior to being combined with the measurement beam with the coupler 5121. Although reference is made to optical fibers to split the reference beam, one of ordinary skill in the art will recognize that this can also be done with beam splitters.

The portion of the optical energy transferred through the optical loop 5111 is transferred to the user's left eye 5109-1 along the measurement arm of the Mach-Zender interferometer. For instance, the optical energy being transferred to the user's eye 5109-1 may pass through the OPD correction module 4940 to perform any optical path distance corrections appropriate to the interferometer of the binocular OCT device 4900. This light may then be scanned across the user's eye 5109-1 via a scanning mirror 5113 of the scanner module 4990 to measure the retinal thickness of the user's eye 5109-1 while the user's eye 5109-1 is fixated on a fixation target 4912-1 (e.g., along a fixation path 5106-1).

The fixation target 4912-1 can be back illuminated with LED 5102-1, and light may be propagated along the optical path 5106-1 through optical elements 5103-1 and 5105-1 and the dichroic mirror 5115, comprising a hot mirror. In some instances, the target of fixation may also include an illumination stop 5104 so as to provide relief to the user's eye 5109-1 while fixating on the target.

The light impinging the user's cornea and retina of the eye 5109-1 may be reflected back along the path established by the OPD correction module 4940, the scanning mirror 5113, the focusing element 5114, the dichroic mirror 5115, and the optical element 4916-1, through the optical loop 5111, and back to the optical coupler 5122. In this instance, the optical coupler 5122 may optically transfer the reflected optical energy to an optical coupler 5121 which may couple the reflected optical energy from the measurement arm with the reference optical energy that was split into the plurality of reference optical paths along loops 5110 and loop 6110. The optical coupler 5121 may then optically transfer that optical energy to the balanced detectors 5101-4 and 5101-5 such that an axial length measurement can be performed. In some embodiments, the measurement comprises corneal thickness measurement and a retinal thickness measurement. In performing the measurement with the balanced detector, the optical coupler 5121 may split that optical energy to approximately 50% to each of the detectors 5101-1 and 5101-4, such that the interference signals arrive out of phase on the balanced detectors.

The light may be focused through a plurality of optical elements 5112 and 5114, being directed to the user's eye 5109-1 via a dichroic mirror 5115 and focused on the user's retina via the optical element 4916-1. The light from the scanning mirror 5113 and the light reflected from the user's eye 5109 are both shown as reflecting off the dichroic mirror 5115, which may comprise hot mirror 4913 configured to generally reflect infrared light and transmit visible light.

As can be seen in this example, the user's right eye 5109-2 does not receive any optical energy from the one or more VCSELs 4952 with the orientation shown. Rather, the user's right eye 5109-2 is used for binocular fixation with the target 4912-2, which can be back illuminated with another LED 5102-2. The target 4912-2 can be of similar size and shape to target 4912-1 and be presented to the eye with similar optics, so as to provide binuclear fixation. In this regard, the user's right eye 5109-2 may also fixate on the target 4912-2 along an optical path 5106-2 through the optical elements 4916-2, 5105-2, 5103-2, and the illumination stop 5104-2, which comprises similar optical power, separation distances and dimensions to the optics along optical path 5106-1.

The binocular OCT system 4900 can be configured to move optical components to a customized configuration for the user being measured. Lens 4916-1 can be adjusted along optical path 5106-1 in accordance with the refraction, e.g. eyeglass prescription, of the eye being measured. Lens 4916-1 can be moved under computer, user or other control to adjust lens 4916-1 to bring the fixation target 4912-1 into focus and to focus the measurement beam of the OCT interferometer on the user's retina. For example, the lens can be translated as shown with arrow 5146. In some embodiments, lens 4916-1 comprises an objective lens, e.g. a lens along the optical path closest to the corresponding eye. Lens 4916-2 can be moved under computer, user or other control to adjust lens 4916-2 to bring the fixation target 4912-2 into focus on the user's retina. For example, the lens can be translated as shown with arrow 5144. In some embodiments, lens 4916-2 comprises an objective lens, e.g. a lens along the optical path closest to the corresponding eye. The OPD correction module 4940 can be translated axially toward and away from mirror 5113 as shown with arrows 5146. The OPD correction module 4940 can be moved under computer control to appropriately position the optical path difference between the measurement arm and the reference arm for the user's eye being measured. The interpupillary distance can be adjusted by translating the optical path 5106-2 toward and away from optical path 5106-1.

The free space optics module 4910-2 may comprise one or more components along optical path 5106-2, such as the LED 5101-2, the fixation target 4912-2, lens 5103-2, aperture 5104-2, lens 5105-2, or lens 4916-2. The free space optics module 4910-2 can be translated laterally toward and away from the optical components located along optical path 5106-1 to adjust the inter pupillary distance as shown with arrow 5142. The free space retinal thickness optics module 4910-1 may comprise one or more components located along optical path 5106-1, such as the LED 5102-1, the fixation target 4912-1, the aperture 5104-1, the mirror 5116, the lens 5105-1, the mirror 5115, or lens 4916-1. The OPD correction module 5146 may comprise the optical fiber of the measurement arm of the interferometer, and lens 5112 to substantially collimate light from the optical fiber and to focus light from the retina into the optical fiber.

Figure 7:
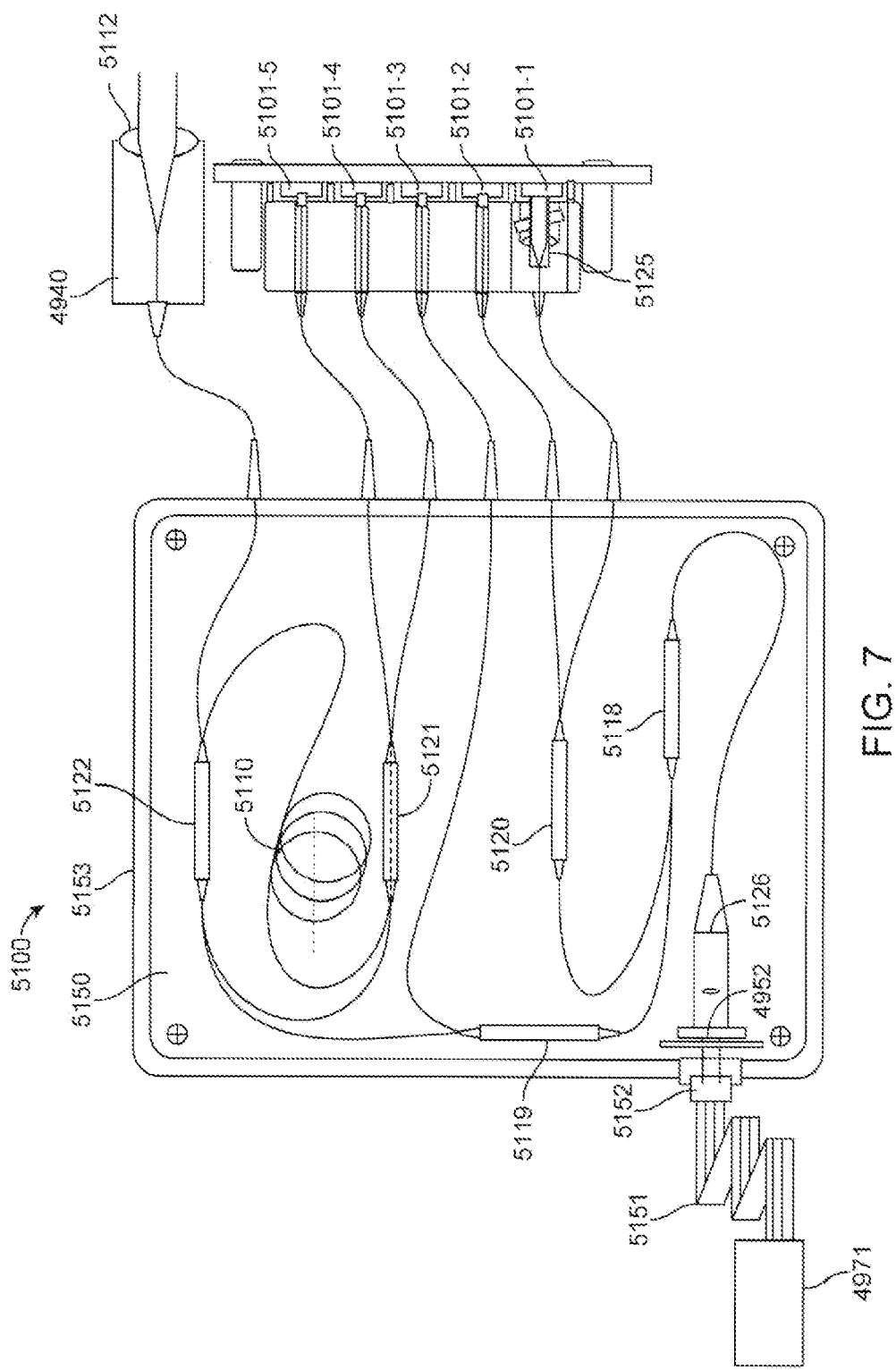
FIG. 7 shows a block diagram of the optical configuration configured on an optical layout board, in accordance with some embodiments.

FIG. 7 shows a block diagram of the optical configuration 5100 configured on an optical layout board 5150, in accordance with some embodiments. For example, the binocular OCT device 4900 may be configured with a plurality of layers extending approximately along planes, each of which layers may be configured to perform a particular function. In this instance, the optical layout board 5150 provides a support for the optical configuration 5100, which can be used to decrease vibrations of the optical components. The optical board 5150 may comprise a plurality of components enclosed within a housing of a fiber optics module as described herein. The plurality of components enclosed within the housing 5153 and supported on the board, may comprise one or more of coupler 5118, coupler 5119, coupler 5120, coupler 5121, coupler 5122, reference arm comprising optical fiber 5110, and any combination thereof. The one or more VCSELs 4952 may be enclosed within the housing. The plurality of optical fibers extending from coupler 5120 can extend through the housing to the appropriate detector, for example to couple to clock box detector 5101-1 and safety detector 5101-2. The optical fiber extending from coupler 5119 can be coupled to a second safety detector 5101-3 and extend though housing 5153. A second optical fiber extending from coupler 5119 can be coupled to the interferometer to measure the sample with optical coupler 5122. The optical fiber portion of the sample measurement arm may extend from coupler 5122 and through the housing 5153 to the optical path difference correction module 4940, for example.

The printed circuit board may provide a support layer extending along an electronics plane in which some processing devices (e.g., the main electronic board 4970 including the driving electronics 4971) could couple to the optical layout board 5150 through a cable 5151 that connects to a connector 5152 configured with the optical layout board 5150 in order to drive one or more VCSELs 4952.

Figure 8:
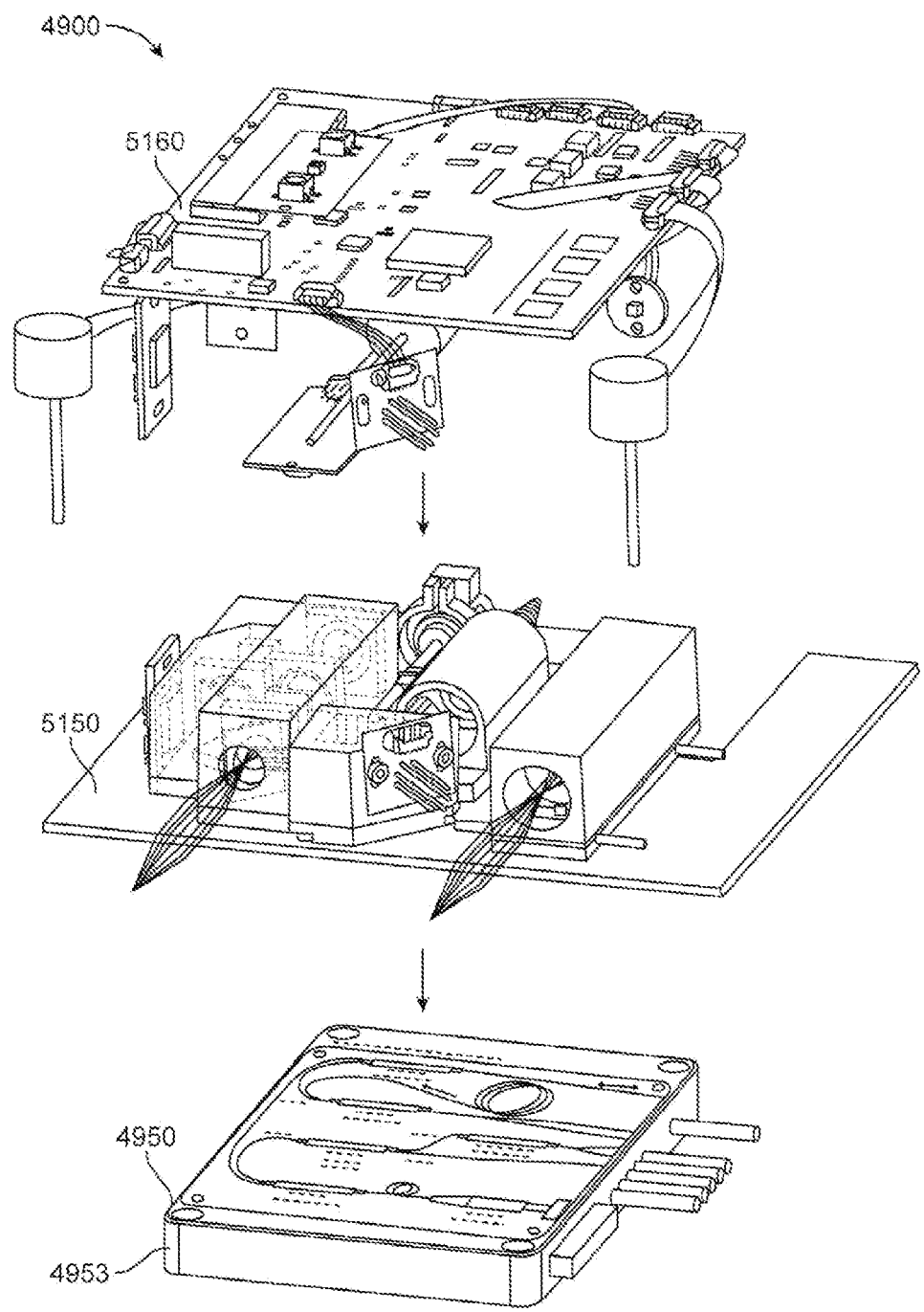
FIG. 8 shows a perspective view of a modular binocular OCT device, in accordance with some embodiments.

FIG. 8 shows a perspective view of a modular embodiment of the binocular OCT 4900, in accordance with some embodiments. For instance, the main electronic board 4970 of the binocular OCT 4900 may be implemented as a printed circuit board (PCB) 5160 that is mounted to a housing 4953 enclosing optical components on the optical layout board 5150. The PCB 5160 may provide the power and electronics to control the optical configuration 5100 of the optical layout board 5150. The PCB 5160 may also include or be communicatively coupled to peripheral boards 4932-1, 4932-2, 4943, 4914-1, and 4914-2. The binocular OCT device 4900 may also comprise free space optics modules that are mounted on the optical layout board 5150 and communicatively couple to the main electronic board 4970. The free space optics modules mounted on the optics board may comprise one or more of module 4910-1, module 4910-2, or OPD correction module 4940 as described herein. The free space module 4910-2 can be configured to move in relation to optical layout board 5150 to adjust the inter pupillary distance. The OPD correction module can be configured to move relative to optical layout board 5150.

The interferometer module 4950 may comprise the couplers of the optical fibers as descried herein and the one or more VCSELs 4952. The main electronic board 4970 or one of the peripheral boards may comprise the electronics that drive the VCSELs 4952. The one or more VCSELs 4952 being optically coupled to the optical fibers on the optical layout board 5150, propagate laser light to the optical fibers on the optical layout board 5150. The laser light reflected from the user's eye 5109-1 can be propagated to the PCB 5160 where the photodetector 4972 detects the reflected laser light and converts the light to an electronic analog signal for processing by the analog block 4974.

In some embodiments, the optical layout board 5150 provides damping to the binocular OCT 4900. For instance, if the binocular OCT 4900 were to be dropped, a damping mechanism configured with the optical layout board 5150 may compensate for any oscillatory effects on impact of the binocular OCT 4900 and protect the components thereof (e.g., the optical layout board 5150, the PCB 5160, interferometer module 4950, and the components of each). The mounting plate 5150 may comprise similar damping mechanisms.

Figure 9:
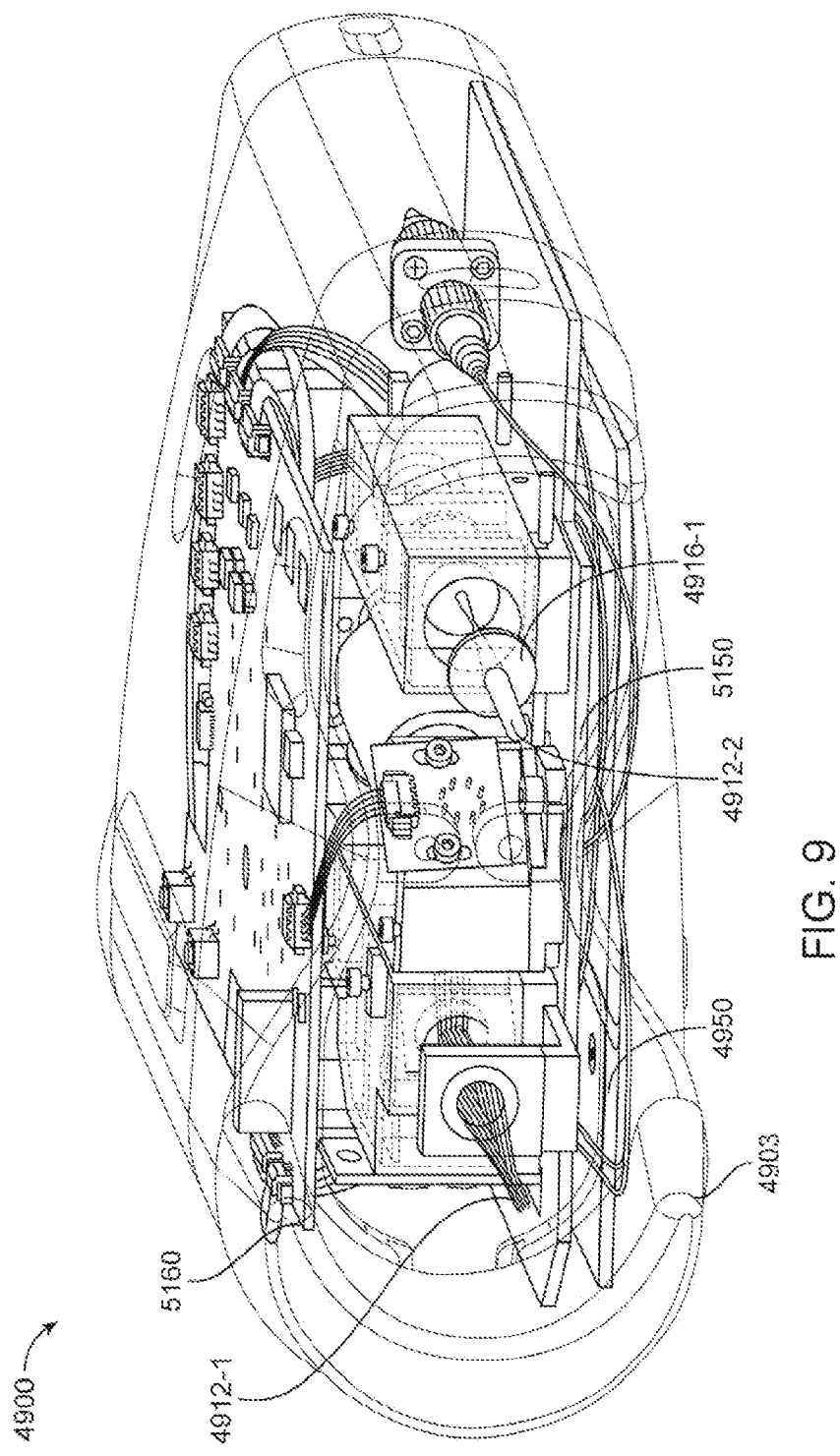
FIG. 9 shows a perspective/cut-away view of the binocular OCT device, in accordance with some embodiments.

FIG. 9 shows a perspective/cut-away view of the binocular OCT 4900, in accordance with some embodiments. In this view, the optical layout board 5150, the PCB 5160, and the interferometer module 4950 are mechanically coupled together in a compact form configured within the housing 4903 of the binocular OCT 4900. As can be seen in this view, the fixation targets 4912-1 and 4912-2 (e.g., LED light) are visible to the user through the lenses 4916-1 and 4916-2, respectively, when the user places the binocular OCT 4900 proximate to the user's eyes. Laser light from the VCSELs propagates along a portion of the same optical path as the fixation target 4912-1. Thus, when the user gazes on the fixation targets 4912-1 and 4912-2, the laser light from the one or more VCSELs as described herein are operable to propagate through the user's eye and reflect back to the optical layout board 5150 for subsequent processing to determine the user's retinal thickness.

Figure 10:
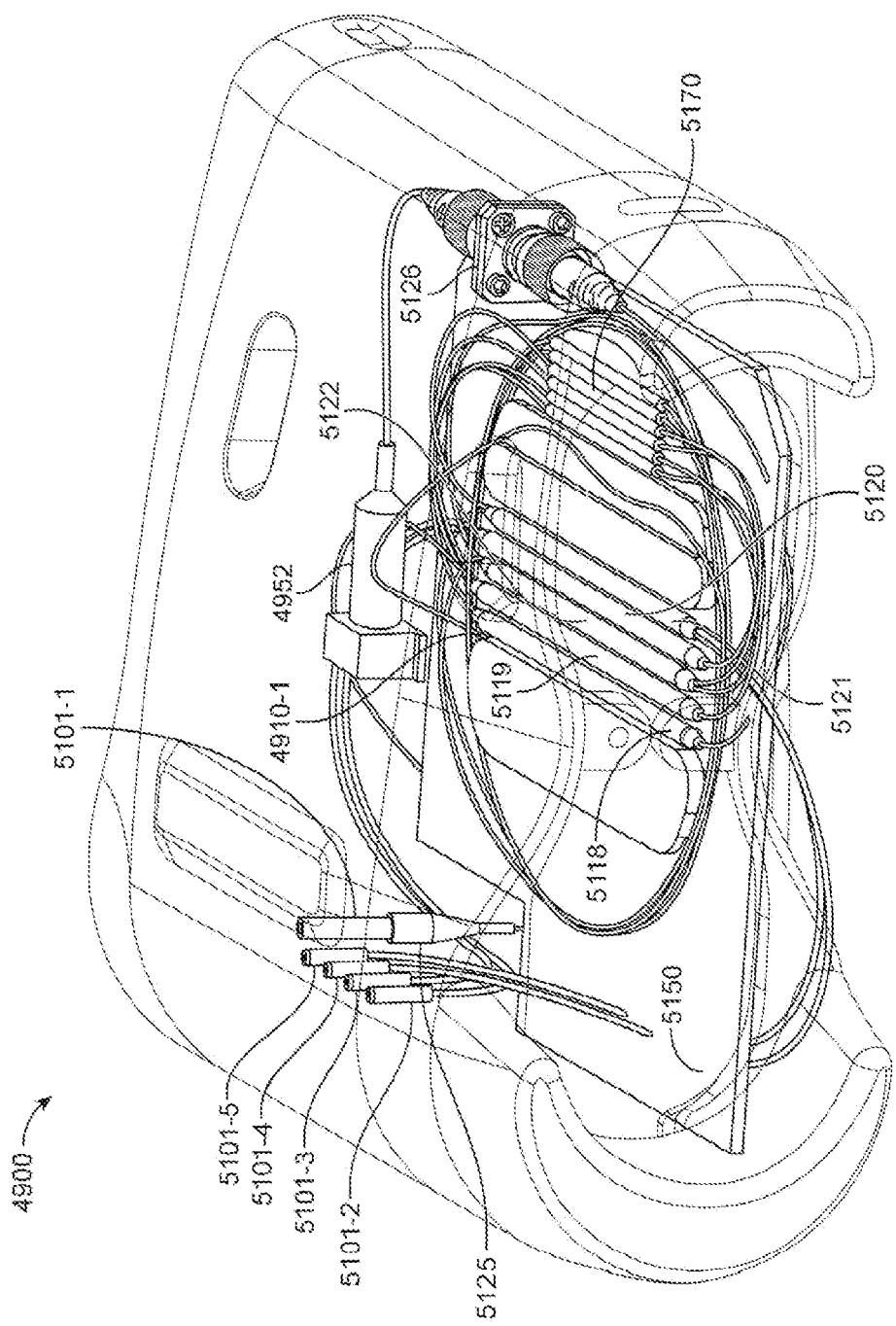
FIG. 10 shows another perspective/cut-away view of the binocular OCT device, in accordance with some embodiments.

FIG. 10 shows another perspective/cut-away view of the binocular OCT device 4900, in accordance with some embodiments. In this view, the optical layout board 5150 is illustrated to show the configuration of the one or more VCSELs 4952, the fiber coupler 5126, the detectors 5105-1-5105-5, the Fabry Perot optical clock 5125, and the optical couplers 5118-5122. The optical layout board 5150 may also comprise splices 5170.

Figure 11:
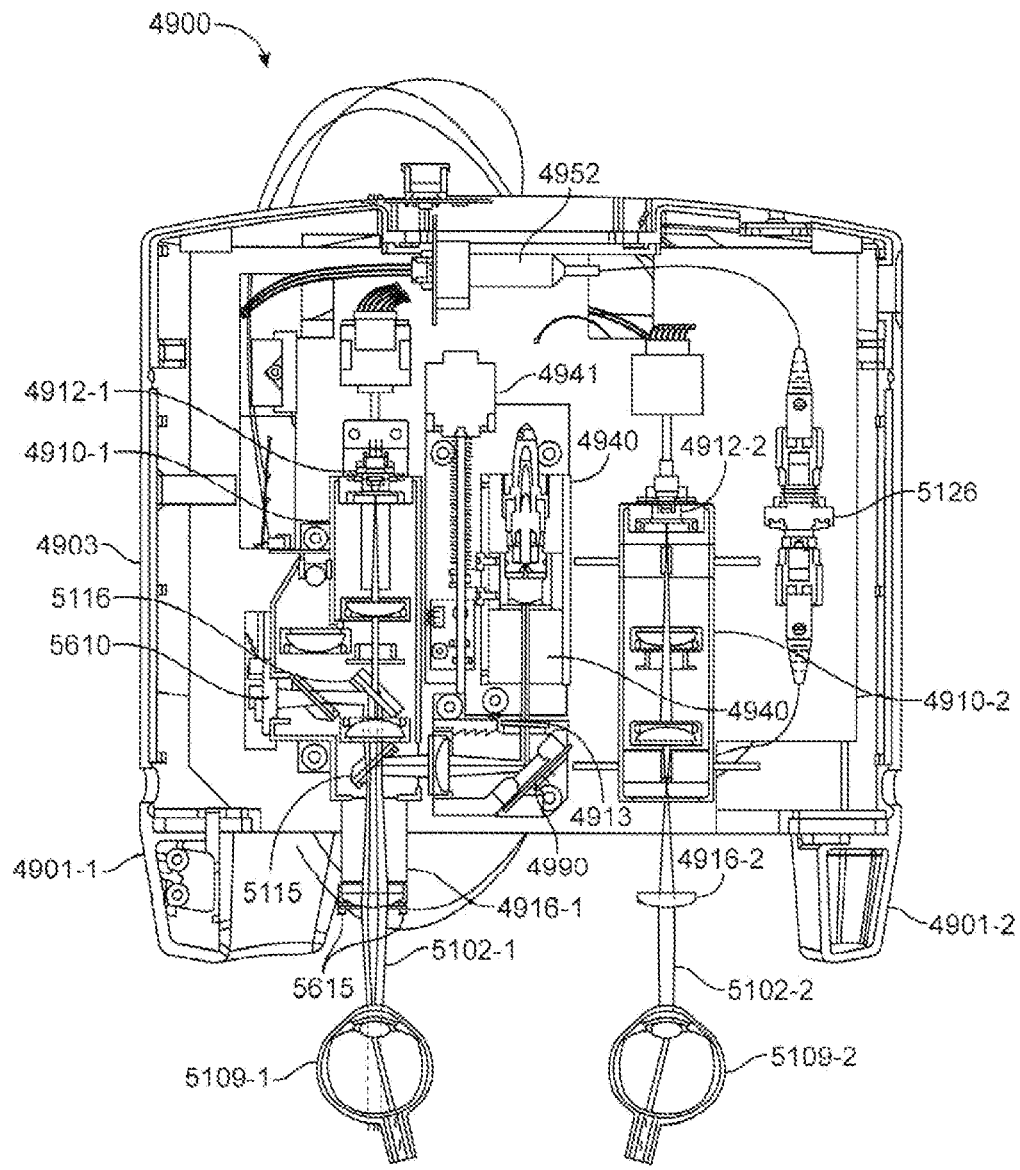
FIG. 11 shows an overhead/cut-away view of the binocular OCT device comprising an eye position sensor, in accordance with some embodiments.

FIG. 11 shows the binocular OCT system 4900 comprising an eye position sensor, in accordance with some embodiments. FIG. 11 shows an overhead/cut-away view of the binocular OCT 4900 comprising an eye position sensor 5610, in accordance with some embodiments. The eye position sensor 5610 may comprise one or more of an array sensor, a linear array sensor, a one dimensional array sensor, a two-dimensional array sensor, a complementary metal oxide (CMOS) two-dimensional array sensor array sensor, a quadrant detector or a position sensitive detector. The eye position sensor 5610 can be combined with a lens to form an image of the eye on the sensor, such as a Purkinje image from a reflection of light from the cornea of the eye. The eye position sensor can be incorporated into any of the embodiments disclosed herein, such as the binocular OCT system described with reference to FIGS. 1B to 10.

In the view shown, the optical configuration 5100 is mounted on the optical layout board 5150 above the fiber-optic couplings (e.g., the fiber loops 5110 and 5111 of FIG. 6) and the optical couplers 5118-5122, and other fiber components as described herein. Thus, the one or more free space optical components as described herein may be optically coupled to the fiber components thereunder.

As shown, the free space optics modules 4910-1 and 4910-2 are generally aligned with the user's eyes 5109-1 and 5109-2, respectively. The distance between the free space optics modules 4910-1 and 4910-2 may be adjusted according to the user's IPD as described herein. In some embodiments, this adjustment is maintained for the user while the binocular OCT 4900 is in the user's possession. For example, the user may be a patient using the binocular OCT 4900 for home use over a period of time. So as to ensure that a correct axial length, corneal thickness and retinal thickness measurements are performed while in the user's possession, the binocular OCT 4900 may prevent the user from adjusting the IPD. Similarly, the binocular OCT 4900 may also prevent the user from adjusting the OPD via the OPD correction module 4940.

As can be seen in this view (FIG. 11), the fixation targets 4912-1 and 4912-2 (e.g., LED light targets) pass through various optical elements of their respective free space optics modules 4910-1 and 4910-2. The OPD correction module 4940 receives the laser light from the one or more VCSELs 4952 and directs light toward the scanning mirror 4990 as described herein. Light from the scanning mirror 4990 passes through a lens and is reflected by a dichroic mirror 5115 to the user's eye 5109-1 through the lens 4916-1.

In some embodiments, the OCT measurement beam remains substantially fixed relative to the position sensor at each of the plurality of positions of the fixation target.

In some embodiments, the axial length map comprises a plurality of regions corresponding to the plurality of positions of the fixation target.

In some embodiments, the axial length map comprises from 5 to 20 regions and the plurality of locations of the fixation target comprises from 5 to 20 regions.

In some embodiments, the OCT system comprises a scanner to scan the OCT beam to a plurality of positions on a patient's retina for each of the plurality of positions of the fixation target. For example, the scanner can be configured to scan an area of the retina with the plurality of retinal positions for each of the plurality of fixation target positions, and the area of the cornea and retina scanned with each of the plurality of fixation target positions is less than an area of the one or more of axial length map, the retinal image, or the corneal image.

In some embodiments, the OCT measurement beam is transmitted to the scanning mirror mounted on a piezo driven motor in order to compensate for the optical path distance. For example, the hot mirror configured to reflect the OCT measurement beam and transmit the fixation target can be configured to translate in order to adjust the optical path difference while the position of the XYZ translation stage remains substantially fixed. In some embodiments, the translation of the mirror will reflect the OCT measurement beam to adjust the OPD while the path of the transmitted light remains substantially unaltered, such as the path of the light from the fixation target and optionally light transmitted through the mirror to the position sensor.

In some embodiments, the OCT beam is routed through a micromirror/microlens assembly, in which both direction and OPD can be adjusted. In some embodiments, the beam radius may also be varied. The micro-optics assembly may be mounted on a set of linear drives, including piezo drives with submicron resolution. Such drives are commercially available from DTI motors as described on the Internet at dtimotors.com.

Such a system may rely on a decreased driving force, so that a driving force of 1N may be sufficient, in accordance with some embodiments.

In some embodiments the driving force is within a range from 0.5 Newtons (N) to 2.5 N, and a resolution does not exceed 0.5 microns. In some embodiments, the response time is 1 mm per 0.1 sec or faster. This lens assembly can be controlled with a processor such as a microcontroller or an FPGA, so as to increase the signal-to-noise ratio as described herein. In some embodiments, the lens assembly is configured to dither the OCT measurement beam on the retina.

As described, the disclosed OCT system includes a scanner that can be controlled to cause a measurement beam to move in a scan pattern on a patient's cornea and retina. The scan pattern may be one of various types, including a stop and go scan pattern, a star scan pattern, a continuous scan pattern, a Lissajous scan pattern, or a flower pattern, sometimes referred to as a rose curve. The flower pattern or rose curve may be used to generate measurement data that can be processed to generate data that represents data that would be obtained from a different scan pattern. Further, the flower pattern or rose curve may be used to generate measurement data that can be processed to generate interferometric data that improves the ability to detect fluid or pockets of fluid in regions of the retina.

Figure 12:
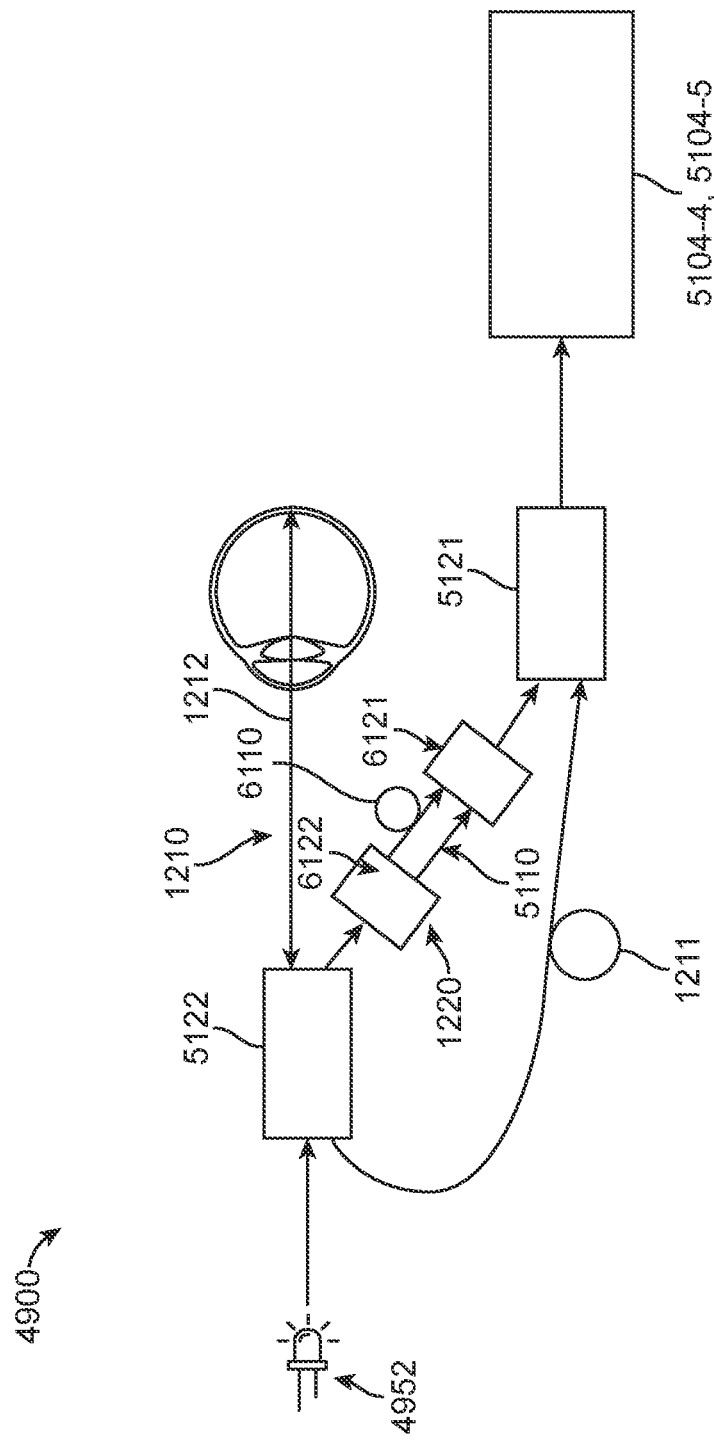
FIG. 12 shows an OCT device with two reference arms, in accordance with some embodiments.

FIG. 12 shows an OCT device 4900 with a plurality of reference arms, e.g. two reference arms, in accordance with some embodiments. The OCT device comprises a light source such as one or more VCSELs 4952. The light source may comprise any suitable light source such as broadband source, a super luminescent diode (SLD), a single VCSEL, a MEMS based VCSEL, a plurality of VCSELs, a plurality VCSELs without MEMS mirrors in which wavelength is swept with overdriving of the VCSEL, an array of VCSELs, or an array of MEMS VCSELs. The OCT device may comprise a plurality of reference optical paths, such as a first reference optical path of a first reference arm to measure a position of the cornea, and a second reference optical path of a second reference arm to measure a position of the retina. The first reference optical path may comprise a first loop 5110 along the first reference optical path and a second loop 6110 along the second reference optical path as described herein. The OCT system may comprise a plurality of couplers to couple optical fibers as described herein. The first and second reference optical paths allow simultaneous measurements of the positions of the retina and cornea as describe herein. The measurement optical path 1210 along a measurement arm of the OCT system may comprise a measurement optical path loop 1211. The portion of the measurement path 1210 extending into the eye may comprise measurement beam 1212.

The light from the reference paths 1220 and the measurement path 1210 can be combined in many ways. In some embodiments, a coupler 6122 splits the reference optical path into the first reference optical path and the second reference optical path, and a coupler 6121 combines the two reference optical paths. A coupler 5121 combines the reference optical path and the measurement optical path, and a plurality of couplers extends from coupler 5121 to balanced detectors 5104-4 and 5104-5 as described herein.

In some embodiments, the OCT device is configured to measure axial length at one location along the eye, for example with a single OCT measurement beam configured to scan the eye without moving a scanning mirror. Alternatively, the OCT system can be configured to scan the measurement beam along the eye as described herein.

In some embodiments, the OCT system is configured to measure the axial length of the eye with a plurality of optical fibers arranged in a substantially fixed configuration. Each of the plurality of optical fibers can be configured to scan a first location of the cornea and a second location of the retina. For example, the OCT device 4900 may comprise a plurality of light sources, interferometers, and detectors, in which the configuration shown in FIG. 12 is duplicated for each of the plurality of measurement beams. In some embodiments, the one or more light sources 4952 comprises an array of VCSELS coupled to a plurality of optical fibers and couplers and detectors, each of which is similar to the configuration of FIG. 12.

Figure 13A:
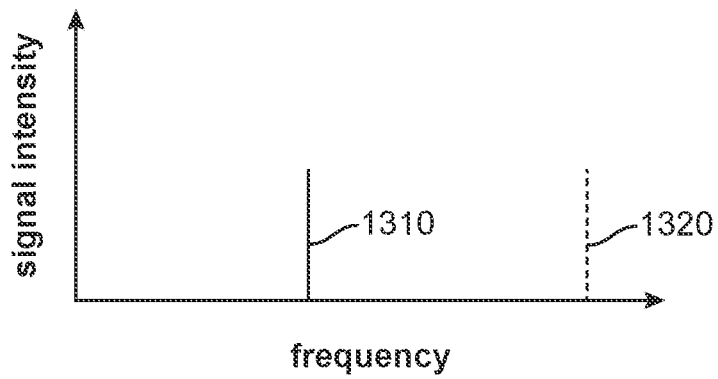
FIG. 13A shows signal intensity and frequency for an OCT device with two signals simultaneously received with one or more detectors, e.g. a balanced pair, in accordance with some embodiments.

FIG. 13A shows signal intensity and frequency for an OCT device with two signals simultaneously received with one or more detectors, e.g. a balanced pair, in accordance with some embodiments. In some embodiments, the frequencies of the interference signal is related to the optical path difference between the reference arm and the sample location along the measurement arm. In some embodiments, the zero optical path difference location is set to a suitable position between the cornea and lens to generate two different frequency bands for the cornea and lens. By positioning the zero optical path difference location such that the distance to the cornea and the distance to the retina are different, two different distributions of frequencies can be obtained, for example with a single reference arm optical path. By positioning the zero optical path difference location closer to the cornea and farther from the retina, the two distributions of frequencies will comprise first lower frequencies corresponding to the position of the cornea at a first location along the measurement optical path and second higher frequencies corresponding to the position of the retina at a second location along the measurement optical path. In some embodiments, a first peak 1310 can occur for a first distribution of frequencies, which correspond to the first optical path difference along the sample measurement arm, e.g. corneal frequencies, and a second peak 1320 can occur for a second distribution of frequencies, which correspond to the second optical path difference along the sample measurement arm, e.g. retinal frequencies. Alternatively, the optical path difference for the cornea can be greater than the retina, such that the corneal frequencies are greater than the retinal frequencies. These signals can be generated with the OCT system comprising a single reference arm or a plurality of reference arms as described herein, for example with reference to FIGS. 6 and 12. In some embodiments, the optical path differences for the cornea and retina are sufficiently different so to provide separation of the distribution of frequencies of the first peak 1310 and the distribution of frequencies of the second peak 1320. In some embodiments, the first reference fiber comprises a first length configured to provide first measurement frequencies for the cornea and the second reference optical fiber comprises a second length configured to provide a second measurement frequencies for retina, in which the first frequencies are resolvable from the second frequencies.

Figure 13B:
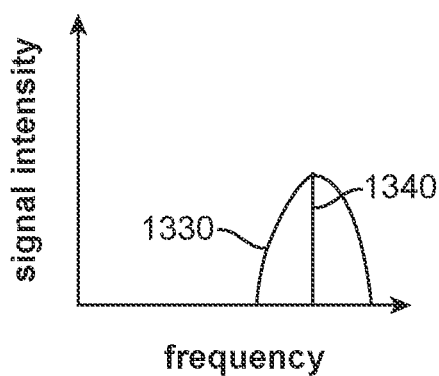
FIG. 13B shows signal frequency broadening due to chirp of the swept source.

FIG. 13B shows signal frequency broadening of a distribution of frequencies 1330 due to chirp of the swept source. In some embodiments, the swept source VCSEL is driven with a non-linear current ramp to narrow the distribution of frequencies 1330 toward an ideal distribution 1340 comprising a narrower distribution of frequencies. This approach is well suited for use with VCSELs that rely on increased heat from overdriving of the current to the VCSEL to sweep the wavelength of the VCSEL.

In some embodiments, the reference arms have different polarizations in order to separate the signals. This has the advantage of decreasing interference between the reference signals.

In some embodiments, one or more lenses, e.g. the objective lens closest to the eye, comprises a bifocal configuration to focus light simultaneously on the retina and the cornea in order to increase the optical signal.

Figure 14:
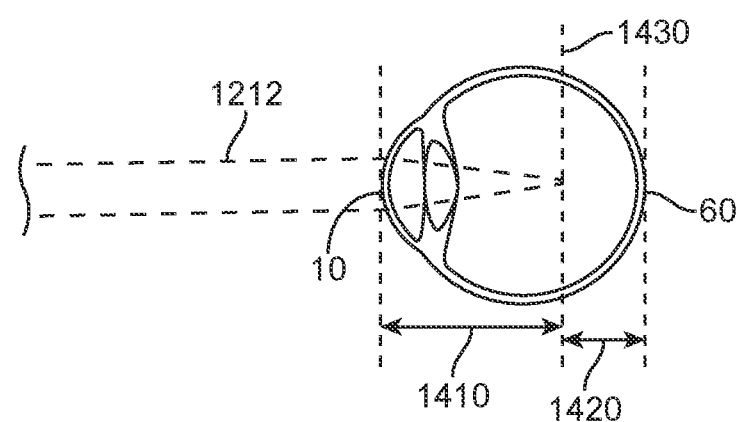
FIG. 14 shows measurement depth of an axial length monitor, in accordance with some embodiments.

FIG. 14 shows measurement depth of an axial length monitor, in accordance with some embodiments. In some embodiments, the axial length monitor comprises a measurement depth that is greater than utilized for retinal measurements. In some embodiments, which measure retinal thickness, the measurement depth is within a range of approximately 8 to 10 mm. The axial length monitor can be configured to measure a suitable distance corresponding to the axial length of the eye, which can correspond to a range from about 29 mm to about 34 mm in air. The coherence length of the light source can be sufficiently long to provide interference of the light source as described herein. In some embodiments, the location of the zero optical path difference 1430 is located between the cornea and the retina, for example between the lens and retina, when the eye is aligned with the OCT measurement system to simultaneously measure the cornea and retina. In some embodiments, the measurement beam 1212 is focused to a waist near the zero OPD location, for example within about 1 mm of the zero OPD location. Alternatively, a bifocal lens can be used to focus the measurement beam on the retina and cornea. A first distance 1410 between the zero optical path difference 1430 and the cornea is measured, and a second distance 1420 between the zero optical path difference ("OPD") between the cornea and retina are measured simultaneously in response to the generated frequencies as described herein. This approach has the benefit of decreasing the measurement depth used to perform the measurement, for example by decreasing the coherence length and number of sampling points used for each A-scan wavelength sweep of the measurement beam. In some embodiments, the first distance 1410 and the second distance 1420 correspond to non-overlapping mirrored interference terms, in which both the corneal surface and retinal surface appear in the image at different distances corresponding to distances from the zero OPD position. In some embodiments, the non-overlapping mirrored interference terms allow each A-scan to be obtained with fewer sampling points as compared to non-mirrored interference terms.

In some embodiments, the reference optical paths are adjusted to set a first zero OPD for the first reference optical path at a first location corresponding to first frequencies from the cornea, and to set the second zero OPD for the second reference optical path at a second location corresponding second frequencies from the retina, in which the first frequencies differ from the second frequencies to be separately resolved. The combined simultaneously generated signals can be separated based on frequencies of the corresponding the reference optical path differences as described herein. This approach can decrease sampling and coherence length of the OCT system to simultaneously measure positions of the cornea and retina.

In some embodiments, the characteristics of interference signals from the cornea differ from the characteristics of interference signals from the retina, and the differences in these characteristics can be used to determine which frequencies correspond to the cornea and which frequencies correspond to the retina. These characteristics may comprise one or more of interference signal intensity or peak sharpness of a distribution of frequencies, for example. In some embodiments, an anterior surface of the cornea provides an interference signal with stronger intensities and a sharper peak of the distribution of frequencies than the intensity and distribution of frequencies from surfaces of the retina, for example.

The measurement beam 1212 can be focused in any suitable manner to measure the cornea and retina and provide measurement signals from the cornea and retina. For example, the measurement beam can be focused between the cornea and retina. Alternatively or in combination, the measurement beam can be focused with a variable lens that changes focus of the measurement beam between the cornea and retina, for example with sequential activation of a lens to a first configuration to focus the measurement beam on the cornea and to a second configuration to focus the measurement beam on the retina. A multi focal lens such as a bifocal lens or a diffractive lens can be used to simultaneously focus the beam on the cornea and retina. In some embodiments, the lens simultaneously focuses on the measurement beam on the cornea and retina and the reference arm comprises the plurality of reference paths as described herein.

Physical Measurement Considerations.
a. The measurement depth in a swept-source OCT is related to following aspects:
  i. Coherent length of the light source;
  ii. Sampling points per wavelength sweep range; and
b. In case of Retinal Thickness Measurement System: (ii) can be a limiting factor Methods to Increase Measurement Depth
a. Increase sampling points per wavelength sweep range by either:
  i. Increasing sampling rate (at constant wavelength sweep rate); or
  ii. Decrease wavelength sweep rate (at constant sampling rate).

In some embodiments, the OCT system is configured to switch between measurement configurations to measure two or more of the following: axial length by measuring the distance between the corneal and the retinal surfaces; retinal thickness; or corneal thickness. In some embodiments, the processor comprises instructions to switch among axial length measurements, retinal thickness measurements, and corneal thickness measurements. Tables 2 and 3 describe measurement parameters that can be used for retinal thickness measurements or axial length measurements, and the processor can be configured to switch among these measurement configurations. Although reference is made to an OCT system that can switch between axial length configurations and retinal thickness configurations, in some embodiments the OCT measurement system is configured to measure axial length without being configured to switch to a retinal thickness measurement configuration.

Table 2 shows measurement parameters for a retinal thickness measurement system configuration and an axial length measurement system configuration. Although approximate parameters are shown in Tables 2 and 3, these values can be decreased by 50% or increased by 100% or more from the values shown, to perform the appropriate measurement. For example, Table 2 shows that by increasing the sampling frequency of from 20 MHz to 80 MHz, the number of sampling points per A-scan from 1000 to approximately 4000, to perform axial length measurements as described herein.

TABLE 2

Measurement Parameters—Approximate Dimensioning for Increased Sampling Frequency.

| Parameter | Retinal Thickness Measurement System | Axial Length Measurement System |
|---|---|---|
| A-sc an repetition rate | 10 kHz | 10 kHz |
| Duration of A-scan | 50 µs | 50 µs |
| Break between A-scans | 50 µs | 50 µs |
| Number of sampling points per A-scan | 1000 | ~4000 |
| Sampling frequency | 20 MHz | 80 MHz |
| Total acquisition duration | 2 s | 2 s |
| Total number of A-scans | 20,000 | 20,000 |
| Scan area on retina | 2 × 2 mm$^2$ | On-axis only or scanned |

Table 3 shows parameters that can be used for measuring retinal thickness and for measuring axial length by using a decreased wavelength sweep rate. In some embodiments, each wavelength sweep corresponds to one A-scan measurement. The duration of a sweep can be increased in accordance with a decrease in the rate of sweeping, to increase the number of sampling points per A-scan. Although the A-scan repetition rate is decreased, the number of A-scan sampling points increases proportionally for a fixed sampling frequency, e.g. 20 MHz. In some embodiments, the measured length along the optical path of the measurement beam, e.g. along the A-scan, is proportional to the number of sampling points per A-scan, such that the measured length of the A-scan along the measurement optical path increases proportionally.

TABLE 3

Approximate Dimensioning for Decreased A Sweep Rate.

| Parameter | Retinal Thickness Measurement System | Approximate Value for Axial Length Measurement |
|---|---|---|
| A-scan repetition rate | 10 kHz | 2.5 kHz |
| Duration of A-scan | 50 μs | 200 μs |
| Break between A-scans | 50 μs | 200 μs |
| Number of sampling points per A-scan | 1000 | ~4000 |
| Sampling frequency | 20 MHz | 20 MHz |
| Total acquisition duration | 2 s | 2 s |
| Total number of A-scans | 20,000 | 5,000 |
| Scan area on retina | 2 × 2 mm$^2$ | On-axis only or scanned |

In some embodiments, the retina position is detected by OCT measurement.

In some embodiments, the cornea position is detected by a position sensor such as 1$^{st}$ Purkinje reflection measurement as described herein.

Both measurements can be approximately simultaneous, e.g. within 100 ms, to decrease measurement inaccuracy related to motion, for example.

Figure 15:
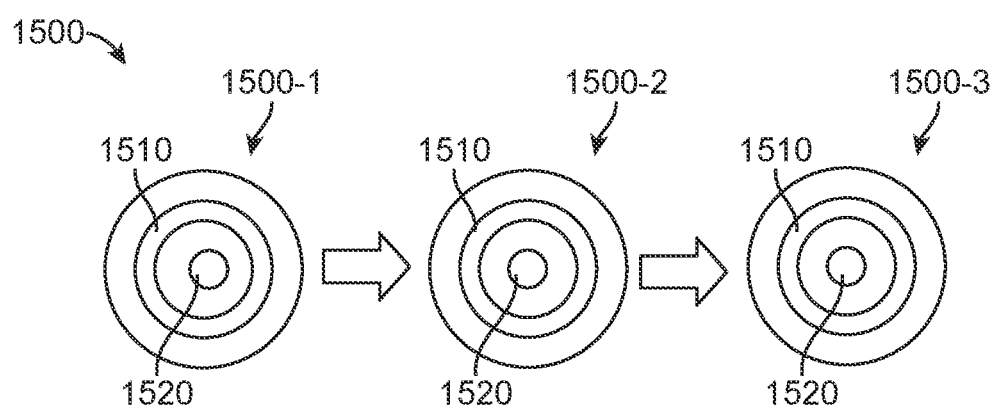
FIG. 15 shows a fixation target configured to change color in response to user alignment, in accordance with some embodiments.

FIG. 15 shows a fixation target 1500 configured to change color in response to user alignment to provide feedback to the user, in accordance with some embodiments. The fixation target 1500 comprises an outer zone such as ring 1510 to indicate coarse alignment and an inner zone such as central dot 1520 to indicate fine alignment. The outer zone may comprise a first color, e.g. red, when the eye is not coarsely aligned with the measurement system and a second color, e.g. green, when the eye is coarsely aligned with the measurement system. The alignment of the eye with the measurement system can be measured in many ways, for example by measuring a position of the eye as described herein. The fixation target 1500 may comprise a first configuration 1500-1 in which the outer zone comprising ring 1510 and inner zone comprising central dot 1520 each comprises a first color such as red to indicate no coarse alignment and no fine alignment. The fixation target 1500 may comprise a second configuration 1500-2 to indicate coarse alignment and no fine alignment. In the second configuration, the outer zone may comprise a second color such as green to indicate the coarse alignment and the inner zone comprises a first color such as red to indicate a lack of fine alignment. A third configuration 1500-3 of the fixation target 1500 may indicate coarse alignment and fine alignment conditions have been met. In the third configuration, the outer zone and the inner zone each comprises the second color, e.g. green. The user can self-align with the system in response to the colors of the fixation target. In some embodiments, once the user is aligned with the OCT measurement system as indicated with third configuration 1500-3, the OCT system will automatically measure the axial length of the eye as described herein.

The fixation target can also be used to provide device status information to the user, for example by blinking or providing other colors. Alternatively or in combination, the OCT system may comprise one or more external indicator lights to provide the device status information. The battery status information indicated by the one or more external indicator lights may comprise one or more of battery status, alignment status, or device status. The battery status information may comprise one or more of charged, currently charging, or low battery level. The alignment status provided by the one or more external lights may comprise not aligned, coarsely aligned, or fine alignment, similarly to the fixation light. The device status provided by the one or more lights may comprise one or more of ready to use, successful acquisition, processing data, or error.

Although reference is made to fixation target to indicate alignment, other approaches can be used, such as one or more of a visual display, voice feedback or voice acquisition.

Figure 16:
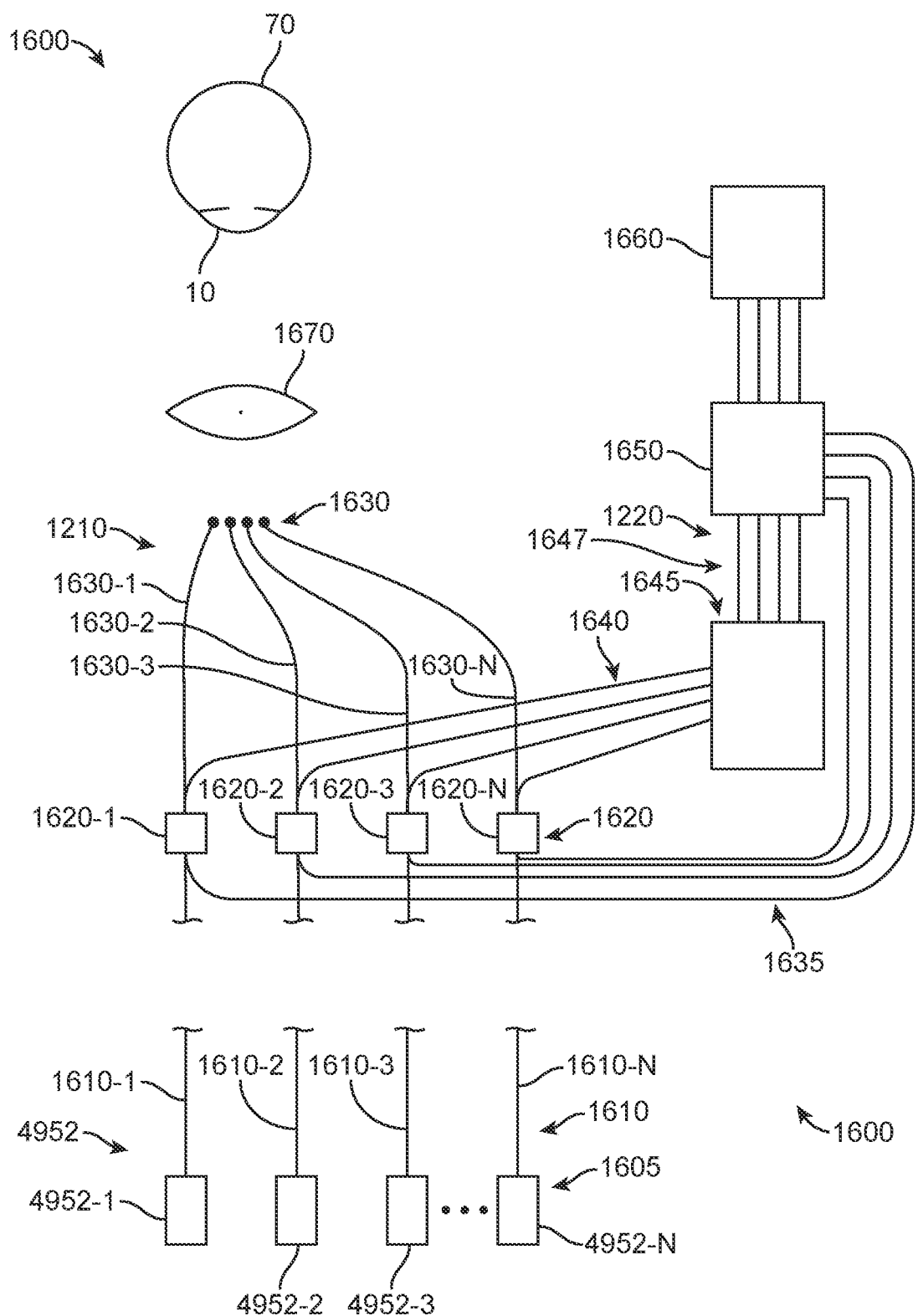
FIG. 16 shows an array of VCSELs coupled to a plurality of optical fibers, in accordance with some embodiments.

FIG. 16 shows a system 1600 comprising a VCSEL array 1605 coupled to a plurality of optical fibers 1610 to measure axial thickness at a plurality of corneal and retinal locations. The plurality of optical fibers 1610 is coupled to a second plurality of optical fibers 1630 comprising distal ends arranged in a pattern to measure the cornea and retina at a plurality of locations as described herein. The plurality of optical fibers 1630 comprises a portion of the measurement arm 1210. The distal ends of the optical fibers 1630 are oriented toward one or more lenses 1670, which focus light from the ends of the optical fibers at a plurality of locations within the eye. In some embodiments, the plurality of corneal and retinal locations is measured without a scanning mirror to scan the beam to the plurality of locations. The light from the retina is focused back into the ends of the optical fibers through lens 1670. The lens 1670 may comprise a mono focal lens, a variable lens, a multifocal or a bifocal lens to focus light between the cornea and retina, on the retina, or on the cornea as described herein.

The plurality of optical fibers 1610 is coupled to the plurality of measurement optical fibers 1630 with a plurality of couplers 1620. The plurality of couplers 1620 receives light from the VCSEL array 1605 and splits the light from the VCSEL array into the optical fibers 1630 of the measurement path and the optical fibers 1640 of the reference path. The reference path comprises a plurality of reference path optical fibers 1645, which may comprise a plurality of split reference paths, in which each of the split reference paths comprises a first distance corresponding to the cornea and a second distance corresponding to the retina as described herein. The plurality of reference path optical fibers comprises a plurality of reference path output optical fibers 1647.

The light from the plurality of reference optical fibers and the plurality of measurement optical fibers is combined with a plurality of couplers 1650 and directed to a plurality of detectors 1660, such as a plurality of balanced detectors as described herein. In some embodiments, the plurality of measurement path optical fibers comprises optical fibers 1635 extending from the plurality of couplers 1620 to the plurality of couplers 1650. The output light from the plurality of couplers 1650 comprises a plurality of interference signals resulting from combination of light from the plurality of measurement path optical fibers 1635 and the plurality of reference path output optical fibers 1647. The light from the plurality of couplers 1650 that is directed to the plurality of plurality of detectors 1660 comprises interference signals in response to sweeping of VCSEL wavelength and can be processed to determine the locations of the cornea and the retina as described herein.

The VCSEL array can be coupled to the optical fibers and detector to generate interference signals in any suitable way. In some embodiments, the VCSEL array comprises one or more light sources 4952 as described herein. The one or more light sources 4952 may comprise an array of VCSELs comprising a first VCSEL 4952-1, a second VCSEL 4952-2, a third VCSEL 4952-3 up to an Nth VCSEL 4952-N. The plurality of optical fibers 1610 may comprise any suitable number of optical fibers, such as a first optical fiber 1610-1, a second optical fiber 1610-2, a third optical fiber 1610-3, up to an Nth optical fiber 1610-N. The plurality of couplers 1620 coupled to the plurality of optical fibers 1610 may comprise any suitable number of couplers, such as a first coupler 1620-1, a second coupler 1620-2, a third coupler 1620-3, up to an Nth coupler 1620-N.

The measurement optical path 1210 can be configured in any suitable way. In some embodiments, the measurement optical path 1210 comprises first measurement optical fibers 1630 and second measurement optical fibers 1635 with the plurality of connectors 1620 coupling the measurement optical fibers. In some embodiments, the first measurement optical fibers comprise a first optical fiber 1630-1, a second optical fiber 1630-2, a third optical fiber 1630-3, up to an Nth optical fiber 1630-N. The second plurality of measurement optical fibers 1635 comprises optical fibers coupled to each of the measurement optical fibers 1630 with the plurality of couplers 1620. The plurality of couplers 1620 may comprise a first coupler 1620-1, a second coupler 1620-2, a third coupler 1620-3, up to an Nth coupler 1620-N.

The number of element up to N as described herein may comprise any suitable number, and N may comprise, 10, 20, 50, 100 or 200, or more elements.

The plurality of reference path optical fibers 1645 and the plurality of couplers 1650 can be configured in any suitable way in accordance with the present disclosure. In some embodiments, the plurality of reference path optical fibers 1645 comprises 2N reference paths, for example when the reference path comprises a first distance corresponding to the cornea and a second difference corresponding to the retina, e.g. N reference paths with the first distance and N reference paths with the second distance. Alternatively, the plurality of reference path optical fibers 1645 may comprise N optical fibers, e.g. comprises the plurality of reference optical fibers 1640, and the plurality of output optical fibers 1647 comprises the plurality of reference path optical fibers 1640. In some embodiments, the plurality of couplers 1650 comprise N couplers, in which each of the plurality of couplers is coupled to one of the plurality of output reference optical fibers 1647 and one of the plurality of measurement optical fibers 1635.

Figure 17:
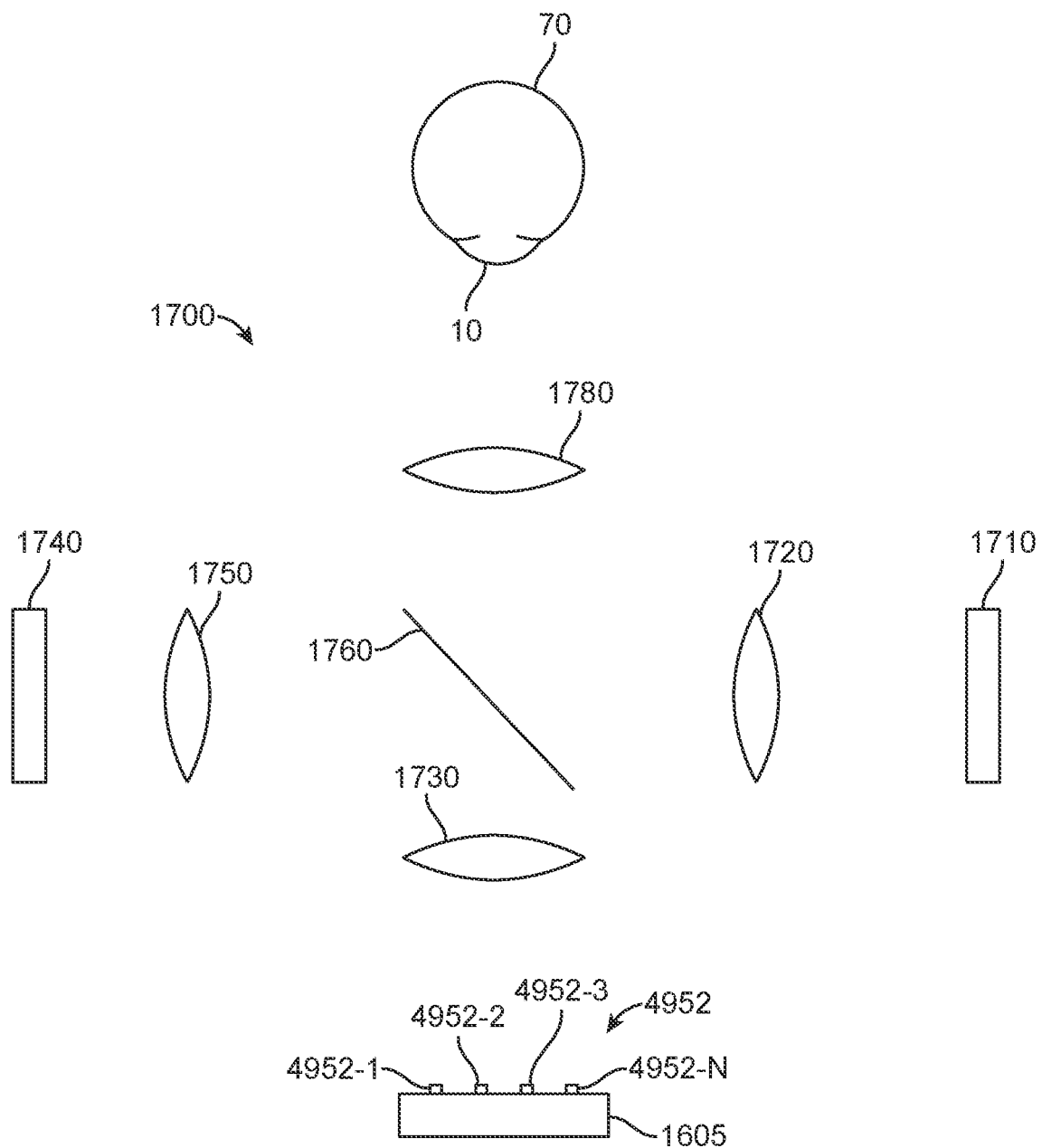
FIG. 17 shows a VCSEL array imaged into the eye, in accordance with some embodiments.

FIG. 17 shows a system 1700 comprising the VCSEL array 1605 imaged into the eye with one or more lenses 1670, and a light received from the eye imaged onto a detector array with one or more lenses after being combined with a reference beam, for example with a Mach-Zender configuration. Light from the VCSEL array 1605 is directed toward one or more lenses 1730, which may substantially collimate light from the plurality of VCSELs. The light from one or more lenses 1730 is directed toward a beam splitter 1760. The beam splitter 1760 reflects a portion of the light along a reference optical path and transmits a second portion of the light along a measurement optical path. The beam splitter 1760 may comprise any suitable beam splitter such as a partially reflective mirror or a polarizing beam splitter for example. A first portion of the light from the beam splitter 1760 is directed toward a mirror 1740 along a reference optical path. Light reflected from mirror 1740 is directed toward beam splitter 1740 and transmitted through the beam splitter 1760 toward detector 1710, which may comprise an array detector such as a complementary metal oxide semiconductor (CMOS) array or a charge coupled device (CCD) array, for example. In some embodiments, one or more lenses 1750 is located between the beam splitter 1760 and mirror 1740.

The portion of light transmitted through beam splitter 1760 is directed along the measurement optical path toward lens 1780 and the eye. The lens 1780 may comprise one or more of a variable focus lens, a multifocal lens, or a bifocal lens, for example. The light transmitted through mirror is imaged inside the eye to form an image of the VCSEL array 1605 within the eye with the optical power of the eye and the lens 1780.

Light returned from the retina is transmitted through lens 1780 and reflected from mirror 1760 toward lens 1720 and detector 1710. The light reflected from mirror 1760 is transmitted through lens 1720 to form an image of the light from the eye on the detector array. In some embodiments, the image of the detector array formed inside the eye is imaged onto the detector array 1710 with lens 1720, such that the image of the VCSEL array is imaged onto the detector. As each of the VCSELs of the array varies the wavelength, the intensity of the corresponding image varies and is captured with detector 1710. Detector 1710 is coupled to a processor and the intensity signal for each VCSEL is captured and processed as described herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

The present disclosure includes the following numbered clauses.

Clause 1. A method of measuring a change in a refractive error of an eye, the method comprising: measuring a first axial length of the eye from a first zone of a retina at a first time to determine a first axial length of the eye, the first zone comprising a first maximum distance across within a first range from about 0.05 mm to about 2 mm; measuring a second axial length of the eye from a second zone of the retina at a second time to determine a second length of the eye at a second time, the second zone comprising a second maximum distance across within a range from about 0.05 mm to about 2.0 mm; wherein the change in refractive error corresponds to a difference between the first axial length and the second axial length.

Clause 2. The method of clause 1, wherein the first maximum distance across is within a range from about 0.1 mm to about 1.5 mm and the second maximum distance across is within a range from about 0.1 mm to about 1.5 mm.

Clause 3. The method of clause 1, wherein the first zone is measured with a first plurality of A-scans of an OCT measurement beam and the second zone is measured with a second plurality of A-Scans of an OCT measurement beam.

Clause 4. The method of clause 3, wherein each of the first zone and the second zone is measured with a scanning OCT measurement beam.

Clause 5. The method of clause 4, wherein the scanning OCT measurement beam moves along a first trajectory to measure the first plurality of A-scans and a second trajectory to measure the second plurality of A-scans.

Clause 6. The method of clause 3, wherein the first zone is measured with a first plurality of fixed measurement beams and the second zone is measured with a second plurality of fixed measurement beams.

Clause 7. The method of clause 6, wherein the first plurality of fixed measurement beams is arranged to generate the first plurality of A-scans and the second plurality of fixed measurement beams is arranged to generate the second plurality of A-scans.

Clause 8. The method of clause 3, wherein the first plurality of A-scans measures a first plurality of corneal locations distributed on a first corneal zone and the second plurality of A-scans measures a second plurality of corneal locations distributed on a second corneal zone and wherein the first axial length corresponds to a difference between the first plurality of retinal locations and the first plurality of corneal locations and the second axial length corresponds to a difference between the second plurality of retinal locations and the second plurality of corneal locations.

Clause 9. The method of clause 8, wherein a first plurality of axial lengths is determined and a second plurality of axial lengths is determined, the first plurality of axial lengths corresponding to first differences between each of the first plurality of corneal locations and a corresponding retinal location, the second plurality of axial lengths corresponding to second differences between each of the second plurality of axial locations and a corresponding retinal location.

Clause 10. The method of clause 1, wherein the first zone substantially overlaps with the second zone and optionally wherein substantial overlap comprises at least about a 50% overlap between the first zone and the second zone.

Clause 11. The method of clause 1, wherein one or more of the first maximum distance across or the second maximum distance across comprises a diameter.

Clause 12. The method of clause 1, wherein one or more of the first zone or the second zone comprises an annulus.

Clause 13. The method of clause 1, wherein one or more of the first zone or the second zone comprises an area.

Clause 14. The method of clause 1, wherein the first axial length comprises a first axial length map and the second axial length comprises a second axial length map and wherein the change in refractive error corresponds to a difference between the first axial length map and the second axial length map.

Clause 15. A system to measure a change in refractive error of an eye, the system comprising a processor configured with instructions to implement the method of any one of the preceding clauses.

Clause 16. The system of clause 15, further comprising: a swept light source to generate an OCT beam and vary a wavelength of the OCT beam; and an interferometer coupled to the swept light source, the interferometer comprising a measurement optical path and a reference optical path, the reference optical path comprising a first reference path and a second reference path; wherein the first axial length corresponds to a first difference between a first position of a cornea of the eye measured with the first reference path and the second reference path measured at a first time and wherein the second axial length corresponds to a second difference between a second position of the cornea measured with the first reference path and a second position of the retina measured with the second reference path at a second time.

Clause 17. The system of clause 16, further comprising a detector coupled to the interferometer to receive a first interference signal and a second interference signal, the first interference signal resulting from light from the first reference path interfering with light from the measurement optical path, the second interference signal resulting from light from the second reference path interfering with light from the measurement optical path.

Clause 18. A system for measuring an axial length of an eye, comprising: a swept light source to generate a light beam and vary a wavelength of the light beam; an interferometer coupled to the swept light source, the interferometer comprising a measurement optical path and a reference optical path, the reference optical path comprising a first reference path and a second reference path; a detector coupled to the interferometer to receive a first interference signal and a second interference signal, the first interference signal resulting from light from the first reference path interfering with light from the measurement optical path, the second interference signal resulting from light from the second reference path interfering with light from the measurement optical path; and a processor coupled to the detector, the processor configured with instructions to determine the axial length of the eye in response to the first interference signal and the second interference signal.

Clause 19. The system of clause 18, wherein the first reference path comprises a first reference optical fiber and the second reference path comprises a second reference optical fiber.

Clause 20. The system of clause 19, wherein the first reference optical fiber comprises a first length and the second reference optical fiber comprises a second length different from the first length.

Clause 21. The system of clause 20, wherein the first length corresponds to a first distance to a cornea of the eye and the second length corresponds to a second distance to a retina of the eye, the first distance less than the second distance.

Clause 22. The system of clause 21, wherein the processor is configured to generate an A-scan comprising a first peak corresponding to the first distance and a second peak corresponding to the second distance for each of a plurality of sweeps of the swept light source.

Clause 23. The system of clause 22, wherein the first interference signal and the second interference signal are received together at the detector for said each of the plurality of sweeps and wherein a transform of time varying intensity data sampled at the detector for said each of the plurality of sweeps generates a first peak corresponding to the first distance and a second peak corresponding to the second distance.

Clause 24. The system of clause 23, wherein the detector comprises a balanced detector.

Clause 25. The system of clause 22, wherein a single sweep of the swept light source generates a first peak and a second peak.

Clause 26. The system of clause 21, wherein the swept light source generates first frequencies and second frequencies at the detector, the first frequencies corresponding to the first reference path length and the second frequencies corresponding to the second reference path length, the first frequencies less than the second frequencies.

Clause 27. The system of clause 21, wherein the first length remains substantially fixed and the second length remains substantially fixed while the swept light source sweeps through a range of wavelengths to measure the first distance and the second distance.

Clause 28. The system of clause 27, wherein the first length corresponds to a first optical path difference along the first reference optical fiber and the second length corresponds to a second optical path difference along the second reference optical fiber, the first optical path difference less than the second optical path difference by an amount within a range from about 16 mm to about 26 mm and optionally within a range from about 18 mm to about 24 mm.

Clause 29. The system of clause 27, wherein the first distance of the first reference optical fiber is less than the second distance of the second reference optical fiber by an amount within a range from about 15 mm to about 25 mm.

Clause 30. The system of clause 18, wherein the first interference signal comprises a first plurality of interference signals from a first plurality of corneal locations and the second interference signal comprises a second plurality of interference signals from a second plurality of retinal locations.

Clause 31. The system of clause 30, wherein the light beam comprises a plurality of measurement light beams at the first plurality of corneal locations and the second plurality of retinal locations.

Clause 32. The system of clause 31, wherein each of the plurality of measurement light beams illuminates a first corneal location and a second retinal location.

Clause 33. The system of clause 31, wherein the first plurality of corneal locations and the second plurality of corneal locations remains substantially fixed when the swept light source sweeps across a range of wavelengths.

Clause 34. The system of clause 33 wherein the plurality of measurement light beams is arranged to measure the cornea at the first plurality of locations and the retina at the second plurality of locations.

Clause 35. The system of clause 31, wherein the swept light source comprises a plurality of swept light sources and the plurality of measurement light beams is generated with the plurality of swept light sources.

Clause 36. The system of clause 35, wherein the plurality of swept light sources comprises a plurality of VCSELs.

Clause 37. The system of clause 36 wherein the plurality of VCSELs comprises two dimensional array of VCSELs.

Clause 38. The system of clause 18, further comprising a mirror configured to scan a measurement beam from the measurement optical path along a retina of the eye.

Clause 39. The system of clause 38, wherein the mirror is configured to scan the measurement beam on the retina over a zone comprising a maximum distance across within a range from about 0.05 mm to about 2.0 mm and optionally within a range from about 0.1 mm to about 1.5 mm and optionally wherein the maximum distance across comprises a diameter.

Clause 40. The system of clause 38, wherein the processor is configured to generate a plurality of A-scans from measurement path at a plurality of locations along the retina and wherein the processor is configured with instructions to determine the axial length in response to the plurality of A-scans.

Clause 41. The system of clause 38, wherein the mirror is configured to scan the measurement beam along a cornea of the eye while the measurement beam scans along the retina of the eye.

Clause 42. The system of clause 41, wherein the processor is configured to generate a plurality of A-scans for locations along the cornea and the retina, each of the plurality of A-scans comprising a first peak corresponding to the cornea and a second peak corresponding to the retina.

Clause 43. The system of clause 42 wherein the processor is configured with instructions to determine a location of the cornea in response to locations of a plurality of corneal A-scan peaks and optionally an angular orientation of the eye with respect to the measurement beam in response to the locations of the plurality of corneal A-scan peaks.

Clause 44. The system of clause 43, wherein the processor is configured with instructions to determine an angular orientation of the eye in response to locations of a plurality of corneal A-scan peaks and a plurality of retinal and A-scan peaks.

Clause 45. The system of clause 44, wherein the processor is configured with instructions to determine the axial length of the eye in response to the angular orientation of the eye.

Clause 46. The system of clause 41, wherein the processor is configured to generate the axial length in response to the plurality of A-scans.

Clause 47. The system of clause 41, wherein the processor is configured to scan the measurement beam along the cornea in a substantially annular pattern.

Clause 48. The system of clause 41, wherein, for each of the plurality of A-scans, a retinal location of the measurement beam is on an opposite side of an optical axis of the eye from a corresponding corneal location of the measurement beam.

Clause 49. The system of clause 48 wherein an objective lens is configured to form an image of the mirror at a location between the cornea and the retina and wherein the measurement beam moves in a first direction on a first side of the image of the mirror toward the cornea and the measurement beam moves in a second direction on a second side of the image of the mirror toward the retina.

Clause 50. The system of clause 38, further comprising an objective lens located between the mirror and the eye, the objective lens configured to focus a measurement light beam to a waist between the retina and a back surface of a lens of the eye, the measurement light beam comprising a portion of the measurement beam.

Clause 51. The system of clause 50, wherein the objective lens is configured to form an image of the mirror in the eye at a location between the cornea of the eye and the retina of the eye and optionally wherein the image of the mirror forms anterior to the waist in the eye.

Clause 52. The system of clause 18, wherein the processor is configured with instructions to generate an axial length map comprising distances between a plurality of corneal locations and a corresponding plurality of retinal locations.

Clause 53. The system of clause 18, wherein a zero optical path difference of the measurement beam is located within the eye between a cornea of the eye and a retina of the eye and wherein the mirror is configured to scan a location of the measurement beam at the zero optical path difference.

Clause 54. The system of clause 18, wherein the first reference path corresponds to a first zero optical path difference and the second reference path corresponds to a second optical path difference.

Clause 55. The system of clause 54, wherein a first location corresponding to the first zero optical path difference of the first reference path is located within about 10 mm of the cornea and a second location corresponding to the second zero optical path difference of the second reference path is located within about 10 mm of the retina of the eye.

Clause 56. The system of clause 55, wherein the first location is scanned with a mirror and the second location is scanned with the mirror.

Clause 57. The system of clause 50, further comprising one or more of a variable focus lens or a bifocal lens to focus the measurement light beam on the cornea and the retina.

Clause 58. The system of clause 18, wherein the swept light source comprises one or more of a laser, a semiconductor laser, a movable mirror coupled to a laser, a micromechanically movable (MEMS) mirror coupled to a laser, a vertical cavity laser, or a vertical cavity surface emitting laser (VCSEL), or a tunable VCSEL with MEMS mirrors.

Clause 59. The system of clause 58, wherein the swept light source comprises the VCSEL, the VCSEL configured to sweep a range of wavelengths with overdriving of a current to the VCSEL.

Clause 60. The system of clause 58, wherein the VCSEL is configured to sweep a range of wavelengths from about 5 nm to about 20 nm and optionally from about 5 nm to about 10 nm.

Clause 61. The system of clause 18, wherein the swept light source comprises a plurality of VCSELs.

Clause 62. The system of clause 18, further comprising a Purkinje imaging system to determine a location of the cornea of the eye.

Clause 63. A system for measuring an axial length of an eye, comprising: an array of VCSELs configured to generate an array of light beams and sweep a wavelength of each of the light beams; an interferometer coupled to the VCSEL array, the interferometer comprising a measurement optical path and a reference optical path to generate a plurality of interference signals; an array detector coupled to the interferometer to receive the plurality of interference signals; and a processor coupled to the detector, the processor configured with instructions to determine the axial length of the eye in response to the plurality of interference signals.

Clause 64. The system of clause 63, further comprising a plurality of optical fibers coupled to the array of VCSELs on proximal ends of the optical fibers and wherein distal ends of the optical fibers are arranged to transmit measurement light beams toward the eye.

Clause 65. The system of clause 63, further comprising a lens configured to image the array of VCSELs inside the eye to generate the plurality of interference signals.

Clause 66. The system of clause 63, wherein each VCSEL of the array is configured to vary the wavelength with one or more heating or an index change of a gain medium within said each VCSEL.

Clause 67. The system of clause 66, wherein said each VCSEL of the array is configured to vary the wavelength without a MEMS mirror.

Clause 68. The system of clause 63, wherein each VCSEL of the array is configured to sweep the wavelength by an amount within a range from about 5 nm to about 20 nm.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system measuring a change in a refractive error of an eye, the system comprising:
    a swept light source to generate a light beam and vary a wavelength of the light beam;
    a scanner comprising a mirror coupled to the swept light source to simultaneously scan a measurement beam along a corneal zone of the eye and a retinal zone of the eye;
    an interferometer coupled to the swept light source and the scanner, the interferometer comprising a measurement optical path and a reference optical path to generate a first plurality of A-scans of the corneal zone and the retinal zone at a first time and a second plurality of A-scans of the corneal zone and the retinal zone at a second time, wherein the first plurality of A-scans and the second plurality of A-scans are generated with a zero point of the measurement optical path and the reference optical path located between a lens of the eye and a retina of the eye;
    a detector coupled to the interferometer to receive the first plurality of A-scans and the second plurality of A-scans from the interferometer; and
    a processor coupled to the detector, the processor configured with instructions to determine a first axial length of the eye in response to the first plurality of A-scans, a second axial length of the eye from the second plurality of A-scans, and the change in refractive error in the eye, wherein the change in refractive error corresponds to a difference between the first axial length and the second axial length.

2. The system of claim 1, wherein the corneal zone of the eye comprises a maximum distance across within a range from about 0.1 mm to about 1.5 mm and the retinal zone of the eye comprises a maximum distance across within a range from about 0.1 mm to about 1.5 mm.

3. The system of claim 1, wherein the processor is configured to move the measurement beam along a first trajectory to measure the first plurality of A-scans and a second trajectory to measure the second plurality of A-scans.

4. The system of claim 1, wherein each of the first plurality of A-scans simultaneously measures a first position of a cornea and a first position of the retina and wherein each of the second plurality of A-scans simultaneously measures a second position of the cornea and a second position of the retina for each of the second plurality of A-scans.

5. The system of claim 1, wherein the first plurality of A-scans measures a first plurality of corneal locations distributed on the corneal zone and a first plurality of retinal locations on the retinal zone and wherein the second plurality of A-scans measures a second plurality of corneal locations distributed on the corneal zone and a second plurality of retinal locations on the retinal zone and wherein the first axial length corresponds to a difference between the first plurality of corneal locations and the first plurality of retinal locations and the second axial length corresponds to a difference between the second plurality of corneal locations and the second plurality of retinal locations.

6. The system of claim 1, wherein the retinal zone comprises a first retinal zone measured with a first plurality of wavelengths and a second retinal zone measured with a second plurality of wavelengths and wherein the first retinal zone overlaps with the second retinal zone with at least about a 50% overlap between the first retinal zone and the second retinal zone.

7. The system of claim 1, wherein the corneal zone comprises a first corneal zone measured with the first plurality of wavelengths and a second corneal zone measured with the second plurality of wavelengths and wherein the first corneal zone overlaps with the second corneal zone with at least about a 50% overlap between the first corneal zone and the second corneal zone.

8. The sytem of claim 1, wherein one or more of the corneal zone or the retinal zone comprises an annulus.

9. The system of claim 1, wherein one or more of the corneal zone or the retinal zone comprises an area.

10. The system of claim 1, wherein the first axial length comprises a first axial length map and the second axial length comprises a second axial length map and wherein the change in refractive error corresponds to a difference between the first axial length map and the second axial length map.

11. The system of claim 1, wherein the swept light source is configured to generate an optical coherence tomography (OCT) beam and vary a wavelength of the OCT beam and the measurement beam comprises an OCT measurement beam.

12. The system of claim 1, wherein the reference optical path comprises a first reference optical path with a first length and a second reference optical path with a second length, the first length different from the second length.

13. The system of claim 12, wherein the first length corresponds to a first distance to a cornea of the eye and the second length corresponds to a second distance to the retina of the eye, the first distance less than the second distance.

14. The system of claim 1, wherein the first plurality of A-scans comprises a first plurality of time varying interference signals and the second plurality of A-scans comprises a second plurality of time varying interference signals.

15. The system of claim 14, wherein the processor is configured to transform each of the first plurality of time varying interference signals to generate first peaks corresponding to the cornea and the retina and wherein the processor is configured to transform each of the second plurality of time varying interference signals to generate second peaks corresponding to the cornea and the retina and wherein the processor is configured to determine the first axial length in response to the first peaks corresponding to the cornea and the retina and determine the second axial length in response to the second peaks corresponding to the cornea and the retina.

16. The system of claim 1, wherein the processor is configured to generate a plurality of A-scans for locations along the cornea and the retina, each of the plurality of A-scans comprising a first peak corresponding to the cornea and a second peak corresponding to the retina.

17. The system of claim 1, wherein, for each of the first and second plurality of A-scans, a retinal location of the measurement beam is on an opposite side of an optical axis of the eye from a corresponding corneal location of the measurement beam.

18. The system of claim 17 wherein an objective lens is configured to form an image of the mirror at a location between the cornea and a back surface of the lens of the eye and configured to focus the measurement beam to a waist between the back surface of the lens and the retina and wherein the measurement beam moves in a first direction on a first side of the image of the mirror toward the cornea and the measurement beam moves in a second direction on a second side of the image of the mirror toward the retina, the first direction opposite the second direction.

19. The system of claim 1, wherein the processor is configured with instructions to generate an axial length map comprising distances between a plurality of corneal locations and a corresponding plurality of retinal locations.

\* \* \* \* \*